United States Patent
Meyerson et al.

(10) Patent No.: US 11,060,148 B2
(45) Date of Patent: Jul. 13, 2021

(54) DIAGNOSING AND TREATING COLORECTAL CANCER

(71) Applicant: DANA-FARBER CANCER INSTITUTE, INC., Brookline, MA (US)

(72) Inventors: Matthew Meyerson, Concord, MA (US); Aleksandar Kostic, Brookline, MA (US)

(73) Assignee: DANA-FARBER CANCER INSTITUTE, INC., Boston, MA (US)

(*) Notice: Subject to any disclaimer, the term of this patent is extended or adjusted under 35 U.S.C. 154(b) by 0 days.

(21) Appl. No.: 14/054,494

(22) Filed: Oct. 15, 2013

(65) Prior Publication Data

US 2014/0107092 A1    Apr. 17, 2014

Related U.S. Application Data

(60) Provisional application No. 61/714,624, filed on Oct. 16, 2012.

(51) Int. Cl.
    C12Q 1/6886    (2018.01)
    C12Q 1/689     (2018.01)

(52) U.S. Cl.
    CPC ........... *C12Q 1/6886* (2013.01); *C12Q 1/689* (2013.01)

(58) Field of Classification Search
    None
    See application file for complete search history.

(56) References Cited

U.S. PATENT DOCUMENTS

2010/0104552 A1*   4/2010   Mygind et al. ............... 424/114
2013/0259899 A1   10/2013   Allen-Vercoe et al.

FOREIGN PATENT DOCUMENTS

WO        2012/045150        4/2012

OTHER PUBLICATIONS

Ray, Katrina. Fusobacterium nucleatum found in colon cancer tissue—could an infection cause colorectal cancer? (Nature Reviews, Gastroenterology & Hepatology, Dec. 2011, vol. 8, p. 662).*
Candoni et al. Fusobacterium nucleatum: a rare cause of bacteremia in neutropenic patients with leukemia and lymphoma. Clin. Microbiol. Infect. 2003; 9: 1112-1115.*
Ott et al. Quantification of intestinal bacterial populations by real-time PCR with a universal primer set and minor groove binder probes: a global approach to the enteric flora. Journal of Clinical Microbiology, Jun. 2004, pp. 2566-2572.*
Walter et al (Microbiol Ecology in Health and Disease 14:129-132, 2002).*
Bennett et al (J Med Microbiol 39:246-254, 1993).*
Casterllarin et al (Genome Res 22:299-306, published online Oct. 18, 2011).*
Marchesi et al (PLoS ONE 6:e20447, published online May 24, 2011) (Year: 2011).*
Rivzi et al (IJCRI 2:16-19, published Jun. 30, 2011) (Year: 2011).*
Werner et al (Visceral Medicine 32:156-157, 2016) (Year: 2016).*
American Cancer Society (available online at https://www.cancer.org/cancer/colon-rectal-cancer/detection-diagnosis-staging/staged.html) (Year: 2019).*
Lofmark et al (Clinical Infectious Diseases 50:S16-S23, 2010) (Year: 2010).*
Kostic et al., The Biology of Cancer: Microenvironment, Metastasis & Therapeutics, Cold Spring Harbor Laboratory, abstract. http://meetings.cshl.edu/meetings/tumbio11.shtml (Apr. 26-30, 2011).
Atarashi et al., "Induction of colonic regulatory T cells by indigenous Clostridium species," Science, 2011, 331:337-341.
Bachrach et al., "Fluorescence based measurements of Fusobacterium nucleatum coaggregation and of fusobacterial attachment to mammalian cells," FEMS Microbiol Lett, 2005, 248(2):235-240.
Bass et al., "Genomic Sequencing of Colorectal Adenocarcinomas Identifies a Recurrent VTI1A-TCF7L2 Fusion," Nat Genet, Sep. 4, 2011, 43(10):964-968.
Boutaga et al., "Peridontal pathogens: a quantitative comparison of anaerobic culture and real-time PCR," FEMS Immunol Med Microbiol, Aug. 1, 2005, 45(2):191-199.
Castellarin et al., "Fusobacterium nucleaum infection is prevalent in human colorectal carcinoma," Genome Research, 2011, 8 pages.
Chang et al., "Identification of herpesvirus-like DNA sequences in AIDS-associated Kaposi's sarcoma," Science, 1994, 266(5192):1865-1869.
Compton, "Colorectal carcinoma: diagnostic, prognostic, and molecular features," Mod Pathol, 2003, 16(4):376-388.
Cover and Blaser, "Helicobecter pylon in health and disease," Gastroenterology, 2009, 136(6):1863-1873.
Dharmani et al., "Fusobacterium nucleatum infection of colonic cells stimulates MUC2 mucin and tumor necrosis factor alpha," Infection and immunity, 2011, 79(7):2597-2607.
Garrity et al., "Taxonomic Outline of the Bacteria and Archae," Taxonomic Outline of the Bacteria release 7.7, 2007, 540-593.
Goodman et al., "Our unindicted coconspirators: human metabolism from a microbial perspective," Cell Metab, 2010, 12(2):111-116.
Han et al., "Interactions between periodontal bacteria and human oral epithelial cells: Fusobacterium nucleatum adheres to and invades epithelial cells," Infect Immun, 2000, 6/(6):3140-3146.
Hope et al., "Sporadic colorectal cancer—role of the commensal microbiota," FEMS Microbiol Lett, 2005, 244(1):1-7.
Kostic et al., "Genomic analysis identifies association of Fusobacterium with colorectal carcinoma," Genome Research, 2011, 7 pages.
Kostic et al., "PathSeq: software to identify or discover microbes by deep sequencing of human tissue," Nature Biotechnology, 2011, 29(5):4-7.

(Continued)

*Primary Examiner* — Craig D Ricci
(74) *Attorney, Agent, or Firm* — McDonnell Boehnen Hulbert & Berghoff LLP

(57) ABSTRACT

Methods for predicting risk of developing colorectal cancer, for treating colorectal cancer, and reducing risk of developing colorectal cancer.

18 Claims, 14 Drawing Sheets

(56) References Cited

OTHER PUBLICATIONS

Loy et al., "probeCheck—a central resource for evaluating oligonucleotide probe coverage and specificity," Environ Microbiol, 2008, 10(10): 2894-2898.
Moore and Moore, "The bacteria of periodontal diseases," Periodontal, 2000, 5:66-77.
Neut et al., "Changes in the bacterial flora of the neoterminal ileum after ileocolonic resection for Crohn's disease," Am J Gastroenterol, 2002, 97(4):939-946.
Okhusa et al., "Ulcerative Colitis: Cliniacal and Experimental. Fusobacterium varium localized in the colonic mucosa of patients with ulcerative colitis stimulates species-specific antibody," J Gastroenterol Hepatol, 2002, 17(8):849-853.
Park, "A Surprising Link Between Bacteria and Colon Cancer," Time Healthland, Oct. 18, 2011, retrieved Oct. 12, 2012, 6 pages.
Polk and Peek, "Helicobacter pylon: gastric cancer and beyond," Nat Rev Cancer, 2010, 10(6):403-414.
Rowland, "The role of the gastrointestinal microbiota in colorectal cancer," Curr Pharm Des, 2009, 15(13):1524-1527.
Sears and Pardoll, "Perspective: alpha-bugs, their microbial partners, and the link to colon cancer," J Infect Dis, 2011, 203(3):306-311.
Stewart et al., "A population-based study of colorectal cancer histology in the United States, 1998-2001," Cancer, Sep. 1, 2006, 107(5):1128-1141.
Strauss et al., "Invasive potential of gut mucosa-derived Fusobacterium nucleatum positively correlates with IBD status of the host," Inflamm Bowel Dis, 2011, 17:1971-1978.
Swidsinski et al., "Acute appendicitis is characterised by local invasion with Fusobacterium nucleatum/necrophorum," Gut, 2011, 60(1):34-40.
Uitto et al., "Fusobacterium nucleatum increases collagenase 3 production and migration of epithelial cells," Infect Immun, 2005, 73(2):1171-1179.
Yang and Pei, "Bacteria, inflammation and Colon Cancer," World J Gastroenterol, 2006, 12(42):6741-6746.
zur Hausen, "Human papillomavirus & cervical cancer," Indian J Med Res, 2009, 130(3): 209.

\* cited by examiner

DNA isolated from colon tissues
(95 tumor-normal sample pairs)

Microbial 16S rDNA

Microbial sequences
(3,700 reads; mean per sample)

DIAGNOSING AND TREATING COLORECTAL CANCER

This application claims the benefit of U.S. Provisional Application No. 61/714,624, filed Oct. 16, 2012, which is incorporated by reference herein.

FEDERALLY SPONSORED RESEARCH OR DEVELOPMENT

This invention was made with Government support under Grant No. RC2CA148317 awarded by the National Institutes of Health. The Government has certain rights in the invention.

TECHNICAL FIELD

This invention relates to methods for diagnosing and predicting risk of developing colorectal cancer, for treating colorectal cancer, and reducing risk of developing colorectal cancer.

BACKGROUND

Malignant tumors are complex communities of oncogenically transformed cells with aberrant genomes, associated non-neoplastic cells including immune and stromal cells, and sometimes microbes, including bacteria and viruses. Several viruses that can integrate into the human genome directly cause cancer, such as human papillomavirus in cervical cancer (zur Hausen 2009) and Kaposi's sarcoma-associated herpesvirus in Kaposi's sarcoma (Chang et al. 1994). In other cases, micro-organisms lead indirectly to cancer through chronic inflammatory responses—a mechanism by which *Helicobacter pylori* contributes to both gastric cancer and MALT lymphoma (Cover and Blaser 2009; Polk and Peek 2010).

In the human distal gut, where microbial cells outnumber host cells nine-to-one (Goodman and Gordon 2010), the microbiome can impart both beneficial and detrimental effects on host physiology contributing to health or disease susceptibility. Gut microbial communities (microbiota) may also influence the development of colorectal carcinoma (Hope et al. 2005; Yang and Pei 2006; Rowland 2009). Sears and Pardoll have recently introduced the concept of the "alpha-bug"—wherein select members of a microbial community, in addition to possessing virulence and pro-carcinogenic features, are capable of remodeling the microbiome as a whole to drive pro-inflammatory immune responses and colonic epithelial cell transformation leading to cancer (Sears and Pardoll 2011, J Infect Dis 203(3): 306-311).

SUMMARY

The tumor microenvironment of colorectal carcinoma is a complex community of genomically altered cancer cells, non-neoplastic cells, and a diverse collection of microorganisms. Each of these components may contribute to carcinogenesis; however, the role of the microbiota is the least well understood. At least in part, the present invention is based on the discovery that *Fusobacterium* can be a proximal cause of colorectal cancer. In addition, *Fusobacterium* are present in stool samples from subjects with colorectal cancer, and substantially absent from healthy subjects.

Thus, in one aspect, the invention provides methods, e.g., in vitro methods, of predicting a subject's risk of having or developing colorectal cancer. The methods include obtaining a stool sample from the subject; detecting a level, e.g. a normalized level, of Fusobacteria, e.g., *F. nucleatum*, in the sample; and comparing the level of Fusobacteria in the sample to a reference level of Fusobacteria; wherein the presence of a level of Fusobacteria, e.g., *Fusobacterium* species, above the reference level indicates that the subject has an increased risk of having or developing colorectal cancer. In some embodiments, the methods include determining that the subject has, or identifying the subject as having, an increased risk of having or developing colorectal cancer if the level of Fusobacteria in the sample is above a reference level of Fusobacteria. In some embodiments, the subject does not have an increased risk of having or developing colorectal cancer if the level of Fuso is below the reference level.

In another aspect, the invention features methods for diagnosing colorectal cancer in a subject. The methods include obtaining a stool sample from the subject; detecting a level, e.g. a normalized level, of Fusobacteria, e.g., *F. nucleatum*, in the sample; and comparing the level of Fusobacteria in the sample to a reference level of Fusobacteria; wherein the presence of a level of Fusobacteria, e.g., *Fusobacterium* species, above the reference level indicates that the subject has colorectal cancer. In some embodiments, the methods include diagnosing the subject with colorectal cancer if the level of Fusobacteria in the sample is above a reference level of Fusobacteria.

In some embodiments, the methods include selecting the subject for treatment if the subject has been diagnosed with colorectal cancer or has an increased risk of having or developing colorectal cancer.

In some embodiments, the methods include administering to the subject a therapeutically effective amount of an antibiotic effective against Fusobacteria, e.g., *F. nucleatum*.

In another aspect, the invention features methods for treating, delaying development of, or reducing risk of developing, colorectal cancer in a subject. The methods include administering to the subject a therapeutically effective amount of an antibiotic effective against Fusobacteria, e.g., *F. nucleatum*.

In a further aspect, the invention features an antibiotic effective against Fusobacteria for use in a method of treating, delaying development of, or reducing risk of developing, colorectal cancer in a subject.

In an additional aspect, the invention provides for the use of an antibiotic effective against Fusobacteria in the manufacture of a medicament for use in a method of treating, delaying development of, or reducing risk of developing, colorectal cancer in a subject.

In some embodiments, the antibiotic is a beta-lactam; penicillin or penicillin derivative; cephalosporin, cephem, or oxacephe; carbapenem; tetracycline or a tetracycline derivative; quinolone or fluoroquinolone; oxazolidinone; lincosamide; chloramphenicol; nitroimidazole or a nitroimidazole antibiotic.

In some embodiments, the antibiotic is administered systemically.

In some embodiments, the antibiotic is administered in an oral composition formulated for delivery to the colon of the subject.

In some embodiments, the antibiotic is administered rectally.

In some embodiments, the antibiotic is formulated to be administered systemically.

In some embodiments, the antibiotic is formulated to be administered in an oral composition formulated for delivery to the colon of the subject.

In some embodiments, the antibiotic is formulated to be administered rectally.

In some embodiments, the subject is a mammalian subject, e.g., a human subject. In some embodiments, the subject has, or has an increased risk of having or developing, colorectal cancer. In some embodiments, the methods include selecting the subject on the basis that they have, or are at increased risk of having or developing, colorectal cancer.

The invention provides several advantages. For example, the stool screening methods are non-invasive and can be performed routinely during an annual examination, to provide early detection of potential risk, and to identify subjects who would benefit from prophylaxis (i.e., to delay progression or development, or reduce risk of developing, colorectal cancer) with an antibiotic that is effective against Fusobacteria as described herein. In addition, the methods can be used to reduce the risk of developing colorectal cancer, e.g., in subjects who have Fusobacteria in the oral cavities and/or stool sample.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

Figure 4A:
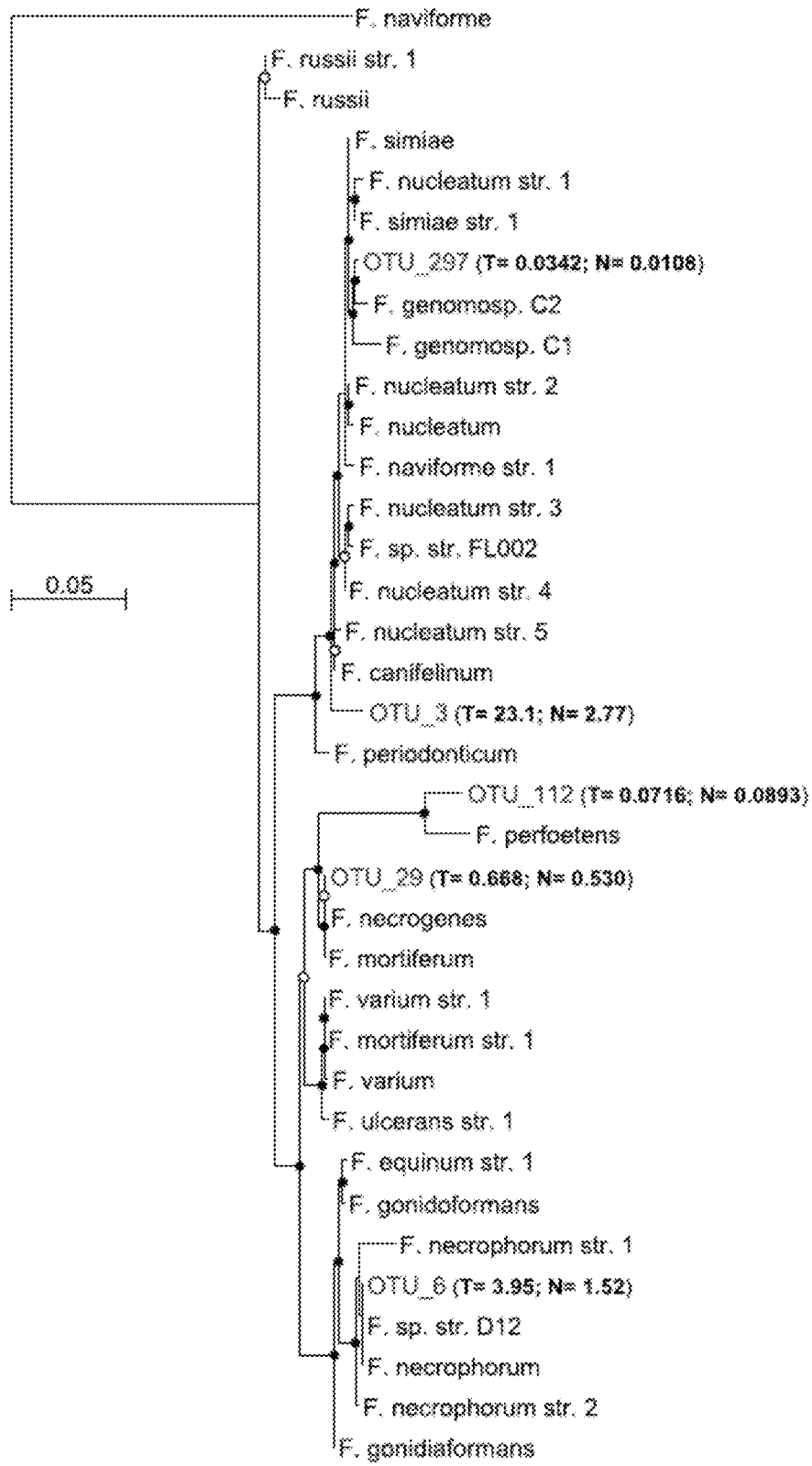
FIGS. 4A-B. Phylogenetic analysis identifies several *Fusobacterium* species in human colon cancer tissues. (4A) Approximately-maximum-likelihood phylogenetic trees were constructed on the V3-V5 region of the 16S rDNA gene using 31 reference *Fusobacterium* species along with the five most prominent OTUs identified in colon cancer specimens (indicated in bold). Nodes that have bootstrap support above 50% and 75% are indicated with a white and black dot, respectively. The mean percent relative abundance in tumor (T) and normal (N) of each OTU is indicated in parentheses. The full names of the reference strains were as follows.

| Designation in FIG. 4A | Greengenes strain name |
|---|---|
| F. naviforme | F. naviforme |
| F. russii str. 1 | F. russii str. ATCC 25533T |
| F. russii | F. russii |
| F. simiae | F. simiae |
| F. nucleatum str. 1 | F. nucleatum fusiforme subsp. fusforme str. NCTC F. russii T |
| F. simiae str. 1 | F. simiae str. ATCC 33568T |
| F. genomosp. C2 | F. genomosp. C2 |
| F. genomosp. C1 | F. genomosp. C1 |
| F. nucleatum str. 2 | F. ATCC 25586 subsp. nucleatum str. JCM 8532 |
| F. nucleatum | F. subsp. nucleatum str. ATCC25586 |
| F. naviforme str. 1 | F. naviforme str. DMS 20699 NCTC 11464 |
| F. nucleatum str. 3 | F. nucleatum subsp. vincentii str. ATCC 49256 |

-continued

| Designation in FIG. 4A | Greengenes strain name |
|---|---|
| F. sp. str. FL002 | F. sp. oral taxon 205 str. FL002 |
| F. nucleatum str. 4 | F. nucleatum str. JC-208 |
| F. nucleatum str. 5 | F. nucleatum ATCC 10953 subsp. polymorphum str. JCM 12990 |
| F. canifelinum | F. canifelinum str. RMA 12708 |
| F. periodonticum | F. periodonticum str. KP-F10 |
| F. perfoetens | F. perfoetens |
| F. necrogenes | F. necrogenes str. ATCC 25556T |
| F. mortiferum | F. mortiferum |
| F. varium str. 1 | F. varium str. NCTC 10560T |
| F. mortiferum str. 1 | F. mortiferum str. ATCC 25557T |
| F. varium | F. varium |
| F. ulcerans str. 1 | F. ulcerans str. NCTC 12111T |
| F. equinum str. 1 | F. equinum str. horse VPB 4027 |
| F. gonidoformans | F. gonidoformans |
| F. necrophorum str. 1 | F. necrophorum str. AB FnS-1 |
| F. sp. str. D12 | F. sp. str. D12 |
| F. necrophorum | F. necrophorum |
| F. necrophorum str. 2 | F. necrophorum subsp. funduliforme str. DSM 19678 |
| F. gonidiaformans | F. gonidiaformans str. ATCC 25563T |

(4B) The abundance of *Fusobacterium* phylotypes relative to all other phylotypes in a given specimen is shown for the two most abundant *Fusobacterium* OTUs in tumors (x-axis) and normal colon tissue (y-axis); each point represents tumor and normal abundance data for a different individual. The lower-right quadrant of the graph highlights the substantial proportion of patients for whom the *Fusobacterium* abundance is >10% in tumors but <10% in the matched normal tissue.

Figure 5:
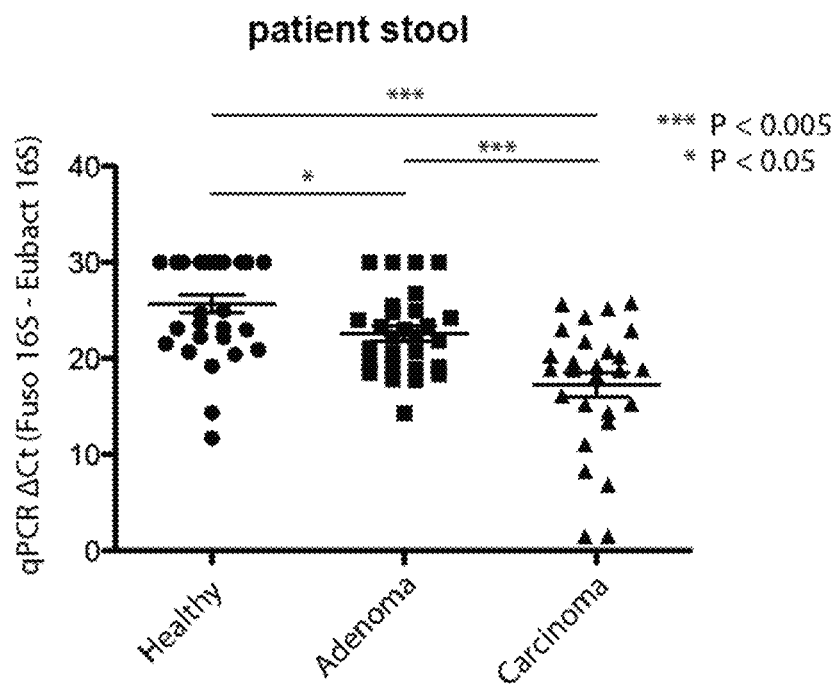

FIG. 5 is a graph showing enrichment in *Fusobacterium* as compared to normal bacterium in stool samples from healthy subjects as well as subjects with colorectal carcinoma or adenocarcinoma.

Figure 6:
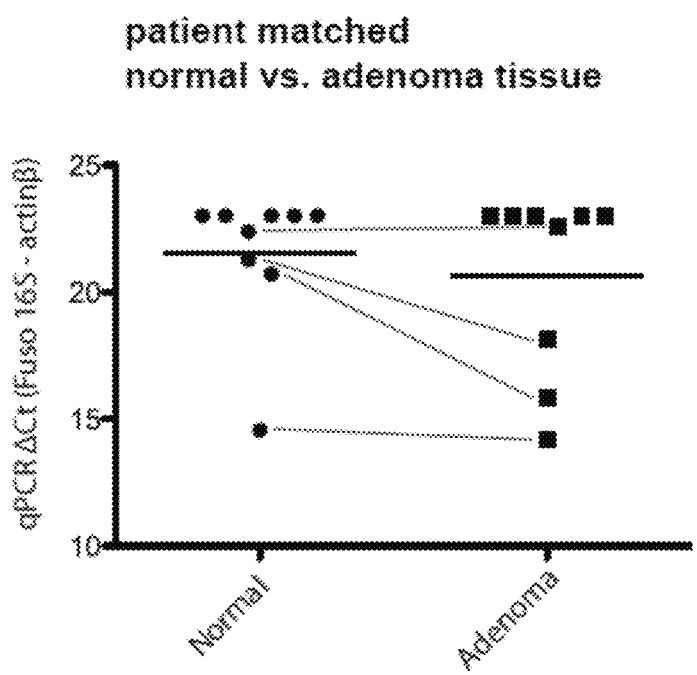

FIG. 6 is a graph showing the levels of enrichment of *F. nucleatum* in colon adenoma tissues as compared to normal control colon tissues in human subjects.

Figure 7:
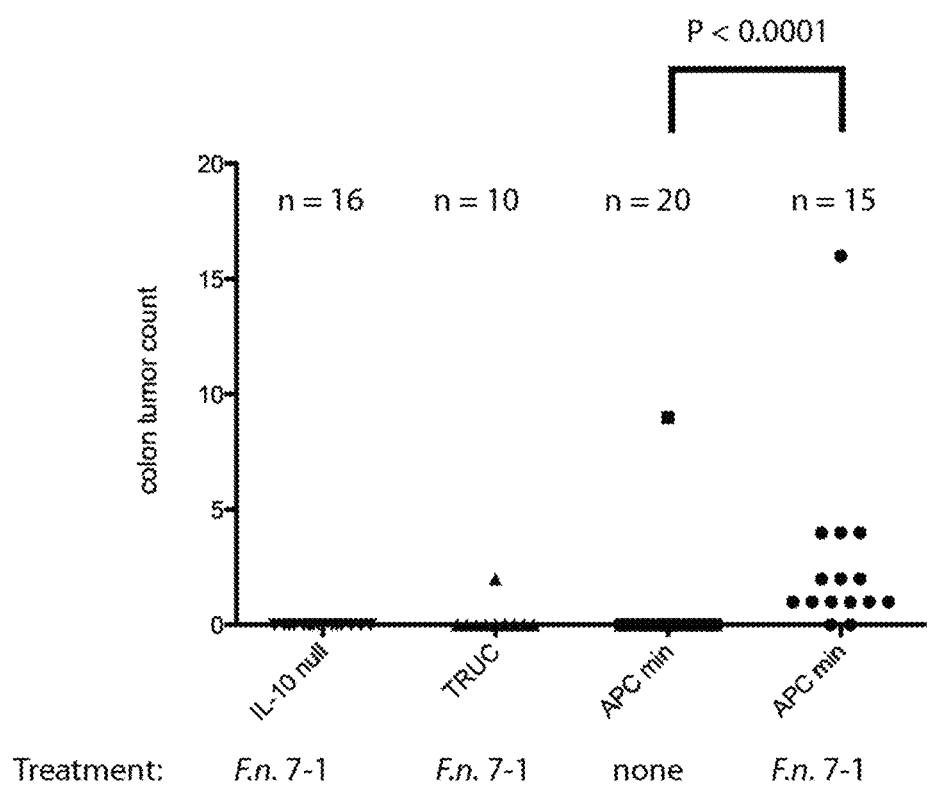

FIG. 7 is a graph showing numbers of colon tumors in mice who were orally administered *F. nucleatum*.

Figure 8:
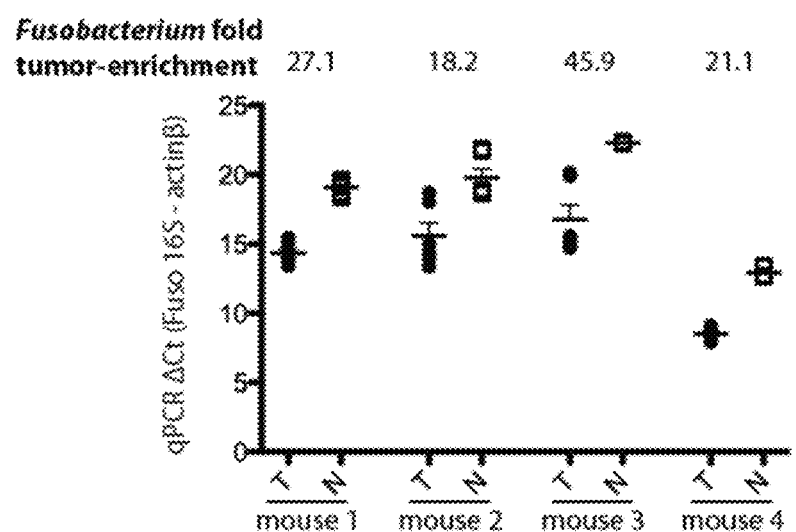

FIG. 8 is a graph showing the levels of enrichment of *F. nucleatum* in colon tumor tissues as compared to normal control colon tissues in mice who were orally administered *F. nucleatum*.

DETAILED DESCRIPTION

The composition of the microbiota in colorectal carcinoma was characterized using whole genome sequences from tumor/normal pairs. As shown herein, *Fusobacterium* sequences were enriched in carcinomas and adenomas, confirmed by quantitative PCR and 16S rDNA sequence analysis of carcinoma/normal and adenoma/normal DNA pairs, while the *Bacteroidetes* and *Firmicutes* phyla were depleted in tumors.

As described herein, genomic analysis of the microbiome of colorectal carcinomas revealed a significant enrichment of *Fusobacterium* species in these cancers, especially phylotypes with the greatest similarity to *F. nucleatum*, *F. mortiferum*, and *F. necrophorum*. This enrichment is confirmed by histological analysis of tumor tissue, and also the identification of *Fusobacterium* DNA in colon tumor metastases. The present analysis also revealed broader changes in the tumor environment such as the depletion of the *Bacteroidetes* and *Firmicutes* phyla, most notably the order Clostridiales. *Fusobacterium* species may have a fitness advantage in the evolving tumor microenvironment resulting in an altered microbiota consistent with the "alpha-bug" hypothesis.

Interestingly, *Fusobacterium* species may be associated with inflammatory bowel diseases (IBD) including both ulcerative colitis and Crohn's disease (Neut et al. 2002; Ohkusa et al. 2002; Strauss et al. 2011), and IBD is a known risk factor, indeed one of three highest risk factors, for colorectal cancer. Furthermore, several *Fusobacterium* strains were associated with IBD, however the majority (69%) were specifically associated with *F. nucleatum* (Strauss et al. 2011).

*F. nucleatum* and other *Fusobacterium* species can elicit host pro-inflammatory response (Moore and Moore 1994) and possess virulence characteristics that promote their adhesiveness to host epithelial cells (Bachrach et al. 2005; Uitto et al. 2005) and their ability to invade into epithelial cells (Han et al. 2000; Strauss et al. 2011).

As described herein, oral administration of an invasive *F. nucleatum* strain, 7-1, lead to the development of tumors in susceptible animals, demonstrating a causal relationship between this microbe and colorectal cancer.

Colorectal Cancer

The methods described herein can be used to screen, diagnose, predict risk of development of, treat, and monitor colorectal cancer in subjects. The subjects are typically mammalian subjects, e.g., human or non-human mammals. As used herein, the term "colorectal cancer" includes both colorectal carcinoma as well as colorectal adenoma.

Screening Methods

As shown herein, the presence of Fusobacteria in a stool sample is associated with the presence of colorectal cancer in a subject. In addition, because Fusobacteria is a causative agent of colorectal cancer, the presence of Fusobacteria in a stool sample indicates that the subject has an increased risk of developing colorectal cancer. Thus, the present methods can be used to diagnose the presence of, or determine risk of developing, colorectal cancer, i.e., adenomas and carcinomas; subjects who have Fusobacteria present in a stool sample at levels above normal have colorectal cancer, have an increased risk of developing colorectal cancer, or an increased likelihood of having colorectal cancer, i.e., adenomas or carcinomas, as compared to subjects who do not have Fusobacteria present in a stool sample, while subjects who do not have Fusobacteria present in a stool sample are less likely to have, and less likely to develop, colorectal cancer, i.e., adenomas or carcinomas, than those who do have Fusobacteria present in a stool sample.

The methods include obtaining a stool sample from a subject, and determining a level of Fusobacteria in the sample. Methods for determining levels of specific bacteria in a sample are known in the art, and can include detecting nucleic acids or proteins that are specific to the bacteria. For example, PCR-based assays such as quantitative PCR can be performed using primers that specifically amplify nucleic acids from *Fusobacterium* species. In some embodiments, the methods include performing bacterial cultivation. Methods for bacterial cultivation are known in the art, and include methods in which stool is smeared onto Fusobacteria-selective agar plates (e.g., plates containing josamycin, vancomycin, and norfloxacin in fastidious anaerobe agar plus 5% defibrinated sheep's blood) and cultured, e.g., for about 96 hours, under strict anaerobic conditions, after which the colonies are quantified and identified by Gram stain. Alternatively, antibodies that bind to Fusobacteria can be used to detect and quantify Fusobacteria in a sample.

The methods can include detecting one or several species of Fusobacteria, e.g., using probes (oligonucleotide or antibody probes) that bind to many or all known species of Fusobacteria, or probes that are more specific to one or a few species. In some embodiments, the methods include using panels of (a plurality of) probes that bind to one or a few species, to allow for detection and identification of which species of Fusobacteria is/are present. When a panel or plurality of probes is used, an array format can be used, e.g., a lab-on-a-chip type assay that can be used to detect multiple species simultaneously in a single sample. In some embodiments, the methods include specifically detecting the presence and/or level of *Fusobacterium* nucleatum sp. In some embodiments, the methods include detecting one or more of *Fusobacterium* nucleatum, *Fusobacterium* necrophorum, *Fusobacterium* mortiferum, and *Fusobacterium* perfoetens.

In some embodiments, the methods include determining a level of a control bacterium, or a level of total bacteria in a sample, to allow the level of Fusobacteria to be normalized across samples.

In some embodiments, the level of Fusobacteria is compared to a reference level of Fusobacteria. Suitable reference levels can be identified by those of skill in the art. For example, in some embodiments the reference level represents a level in a normal healthy subject who does not have colorectal cancer, and does not have an increased risk of developing colorectal cancer; thus the presence of a level above that reference level indicates that the subject has, or is at risk of developing, colorectal cancer. Reference levels can be determined by methods routine in the art, and can be, e.g., a median level, threshold level, a cutoff level for a selected group of subjects, e.g., subjects who represent the top tertile, quartile, 20%, 10%, or 5% of subjects (i.e., subjects who have more Fusobacteria present in their stool than the lower two tertiles, three quartiles, 80%, 90%, or 95%), where the presence of a level of Fusobacteria above that reference level is associated with a statistically significantly increased risk of having or developing colorectal cancer. In some embodiments, the reference level is a range, and the presence of levels below the bottom of the range indicates the absence or low risk of colorectal cancer; the presence of levels within the range indicate a risk of developing colorectal cancer; and the presence of levels above the range indicate the likely presence of colorectal cancer. In some embodiments, the reference level is a level in a control sample that does not have Fusobacteria present, i.e., the presence of any detectable Fusobacteria would be above the reference level. In general, where the level of Fusobacteria is normalized, the reference level will also be similarly normalized.

The methods described herein can be used in combination with one or more other methods of making a diagnosis or determining risk of developing colorectal cancer; such methods are known in the art and include imaging studies (e.g., colonoscopy, CT colonography), fecal occult blood testing (e.g., Hemoccult II, Hemoccult SENSA), and fecal DNA mutation detection (e.g., detection of mutations in APC, K-ras, DCC, p53).

In some embodiments, the methods further include obtaining a biopsy specimen of a colon tumor, and confirming a diagnosis of colorectal cancer based on methods known in the art, e.g., histological examination. See, e.g., Compton, Mod Pathol 2003; 16(4):376-388, and Stewart et al., Cancer. 2006 Sep. 1; 107(5 Suppl):1128-41, and references cited therein.

Methods of Treatment

Furthermore, oral administration of Fusobacteria to mice results in development of colorectal cancers, thus, the present methods can be used to treat, delay development, or reduce risk of developing colorectal cancer in a subject, by administering to the subject an antibiotic that targets Fusobacteria, e.g., administering an antibiotic to the colon of the subject. These methods can further include detecting the presence of Fusobacteria in a stool sample from a subject, e.g., using a method described herein, and optionally selecting a subject who has Fusobacteria in their stool.

Methods of Monitoring Efficacy of Treatment

In some embodiments, the methods described herein are used to determine the efficacy of a treatment administered to a subject. For example, a first level of Fusobacteria in a first sample from a subject, e.g., a stool sample or a sample of colon tissue (e.g., tumor tissue or tissue adjacent to a tumor) is obtained and a level of Fusobacteria is determined. One or more doses of a treatment (e.g., using an antibiotic that is effective against Fusobacteria) is then administered, and a second level of Fusobacteria is determined in a second sample (preferably of the same type as the first sample) from a subject. A decrease in the level of Fusobacteria from the first to the second sample indicates that the treatment has been effective in treating, delaying progression or development, or reducing risk of developing colon cancer.

Furthermore, the present methods can be used to determine whether a treatment has been effective, e.g., by detecting a decrease in levels, or an absence (e.g., undetectable levels) of Fusobacteria in a sample (e.g., a stool sample) from the subject after administration of (one or more doses of) an antibiotic. The treatment with the antibiotic can be repeated, e.g., with the same or an increased dose, and/or with the same or a different antibiotic, until a desired level of *Fusobacterium* in the stool sample (e.g., an undetectable level) is reached.

Antibiotics

The methods described herein can include the administration of an antibiotic that is effective against Fusobacteria to treat, delay progression or development, or reduce the risk of developing colorectal cancer.

An antibiotic that is effective against Fusobacteria is an antibiotic that can kill (bacteriocidal) or significantly reduce proliferation (bacteriostatic) of a Fusobacteria species. Preferably the antibiotic is bacteriocidal (i.e., kills the Fusobacteria). In some embodiments, the antibiotic is effective against a wide spectrum of species; in some embodiments, the antibiotic is effective against *F. nucleatum*. An effective amount of such an antibiotic is a dose sufficient to kill or significantly reduce proliferation of the Fusobacteria in a subject, i.e., a dose that achieves the desired therapeutic or prophylactic effect. A therapeutically effective amount of an antibiotic (i.e., an effective dosage) depends on the antibiotic selected, and can be readily determined by one of skill in the art.

An effective amount can be administered in one or more administrations, applications or dosages. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

A number of antibiotics that are effective against Fusobacteria are known in the art, including beta-lactam antibiotics that include a β-lactam nucleus in their molecular structures, e.g., penicillin and penicillin derivatives (penams), cephalosporins (cephems), monobactams, and carbapenems. In some embodiments, the methods include determining whether the Fusobacteria present in the subject express β-lactamase, an enzyme that attacks the β-lactam ring; in cases where the presence of Fusobacteria that express β-lactamase is detected, non-β-lactam antibiotics can be used, or alternatively, β-lactam antibiotics can be administered with a β-lactamase inhibitor such as clavulanic acid, sulbactam, or tazobactam. In some embodiments, clavulanic acid or clavulanate is administered with amoxicillin (AUGMENTIN) or ticarcillin (TIMENTIN); Sulbactam is administered with ampicillin (UNASYN); or Tazobactam is administered with piperacillin (ZOSYN). In some embodiments, β-lactam antibiotics are co-administered with a β-lactamase inhibitor even if the presence of β-lactamase-expressing Fusobacteria is not detected or not tested for.

In some embodiments, the antibiotic is a penicillin or penicillin derivative, e.g., has a core structure with the molecular formula R—$C_9H_{11}N_2O_4S$, where R is a variable side chain; penicillins and penicillin derivatives include penicllin G, Bicillin C—R/L-A, Pfizerpen, Wycellin, phenoxymethylpenicillin, benzylpenicillin, ampicillin, flucloxacillin, dicloxacillin, methicillin, carbenicillin, ticarcillin, piperacillin, mecillinam (amdinocillin, COACTIN), or pivmecillinam.

In some embodiments, the antibiotic is a cephalosporin, cephem, or oxacephem, e.g., Cefacetrile (cephacetrile), Cefadroxil (cefadroxyl; Duricef), Cephalexin (cephalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefamandole, Cefuzonam, Cefmetazole, Cefotetan, Cefoxitin, cephalosporins: Carbacephems: loracarbef (Lorabid); Cephamycins: cefbuperazone, cefinetazole (Zefazone), cefminox, cefotetan (Cefotan), cefoxitin (Mefoxin), Cefcapene, Cefdaloxime, Cefdinir (Zinir, Omnicef, Kefnir), Cefditoren, Cefetamet, Cefixime (Zifi, Suprax), Cefinenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Fortum, Fortaz), latamoxef (moxalactam), Cefclidine, Cefepime (Maxipime), Cefluprenam, Cefoselis, Cefozopran, Cefpirome (Cefrom), Cefquinome, flomoxef, Ceftobiprole, or Ceftaroline.

In some embodiments, the antibiotic is a carbapenem, e.g., Imipenem (which can be co-administered with a dehydropeptidase inhibitor, e.g., cilastatin); Meropenem, Ertapenem, Doripenem, Panipenem/betamipron, Biapenem, Razupenem or Tebipenem.

In some embodiments, the antibiotic is tetracycline or a tetracycline derivative, e.g., a subclass of polyketides having an octahydrotetracene-2-carboxamide skeleton, e.g., tetracycline, chlortetracycline, oxytetracycline, demeclocycline, semi-synthetic doxycycline, lymecycline, meclocycline, methacycline, minocycline, or rolitetracycline; or a glycylcycline antibiotic, e.g., tigecycline.

In some embodiments, the antibiotic is a quinolone or fluoroquinolone antibacterial agent, e.g., cinoxacin, flumequine, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, prulifloxacin, garenoxacin, delafloxacin, or JNJ-Q2.

In some embodiments, the antibiotic is a oxazolidinone, e.g., linezolid (ZYVOX), Posizolid, Torezolid, Radezolid (RX-1741), or cycloserine.

In some embodiments, the antibiotic is a lincosamide antibiotic, e.g., lincomycin or clindamycin.

In some embodiments, the antibiotic is chloramphenicol.

In some embodiments, the antibiotic is nitroimidazole or a nitroimidazole derivative, e.g., metronidazole, tinidazole, or nimorazole.

Antibiotic Compositions

The methods described herein include the manufacture and use of pharmaceutical compositions, which include antibiotics that are effective against Fusobacteria as active ingredients, e.g., as described herein. Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., as described above.

Pharmaceutical compositions are typically formulated to be compatible with its intended route of administration. Examples of routes of administration suitable for use in the present methods include parenteral, e.g., intravenous, intradermal, subcutaneous, oral, transmucosal, and rectal administration. In some embodiments, the method of administration is intended to deliver a therapeutically effective dose to the colon and/or rectum of the subject. In some embodiments, the method of administration is intended to deliver a therapeutically effective dose to the oral cavity of the subject. In some embodiments, the methods include detecting the presence of Fusobacteria, e.g., *F. nucleatum*, in a sample from the oral cavity of a subject, and administering a dose of an antibiotic to the subject that is sufficient to reduce or eliminate Fusobacteria from their oral cavity, thereby reducing their risk of developing colorectal tumors.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The pharmaceutical compositions can also be prepared in the form of suppositories (e.g., with conventional suppository bases such as cocoa butter and other glycerides) or retention enemas for rectal delivery.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. In some embodiments, the therapeutic compounds are formulated for oral administration with an enteric coating, e.g., methyl acrylate-methacrylic acid copolymers; cellulose acetate succinate; hydroxy propyl methyl cellulose phthalate; hydroxy propyl methyl cellulose acetate succinate (hypromellose acetate succinate); polyvinyl acetate phthalate (PVAP); methyl methacrylate-methacrylic acid copolymers; sodium alginate and stearic acid.

In preferred embodiments, antibiotics for oral administration are formulated with a colon specific drug delivery system (CDDS), e.g., are formulated to be delivered to the colon, e.g., as described in Philip and Philip, Oman Med J. 2010 April; 25(2): 79-87; Rajpurohit et al., Undian J Pharm Sci. 2010 November-December; 72(6): 689-696; Kumar and Mishra, Curr Drug Deliv. 2008 July; 5(3):186-98. Thus the present invention can include compositions comprising an antibiotic that is effective against Fusobacteria, wherein the composition is formulated for delivery to the colon, as well as the use thereof in the present methods.

The pharmaceutical compositions can be included in a container, pack, or dispenser together with instructions for administration.

EXAMPLES

The invention is further described in the following examples, which do not limit the scope of the invention described in the claims.

Example 1

Genomic Analysis Identifies Association of *Fusobacterium* with Colorectal Carcinoma This example describes an unbiased, sequence-based approach, followed by cytological analysis, to probe the differences in the microbial composition of the colorectal carcinoma tumor microenvironment relative to adjacent non-neoplastic tissue.

Materials and Methods

DNA Extraction, Whole Genome Sequencing, and Analysis

DNA was extracted from colorectal carcinoma tumors and adjacent non-affected tissues and whole genome sequencing was performed as described previously (Bass et al.). Initial alignments to the human reference genome were performed as described (Bass et al.). All unaligned sequencing reads were (1) analyzed on PathSeq and (2) aligned to the complete set of fully sequenced bacterial and archaeal genomes (ftp.ncbi.nih.gov/genomes/Bacteria, downloaded 2010 Oct. 7) by MegaBlast (Blast Tools version 2.2.23, word size 16, match reward 1, mismatch reward −2, gap open reward −5, gap extension reward −2). The top 30 sequence matches with >90% sequence identity and >90% query coverage were reported for each read (i.e. query). Classifications were performed at the domain, then phylum, then genus, then species level requiring unique alignments (i.e. reads with equivalent E-values to multiple taxa were removed from analysis). At the species level, relative abundance (RA) for each organism was calculated as follows: RA=(# unique alignment positions in genome*1,000,000)/(# total alignable reads*genome size). The RA values were then per-sample normalized such that the total relative abundance for each sample sums to one. The resulting normalized RA matrix was analyzed on LEfSe (Segata et al.).

Amplification and 454 Sequencing of 16S Gene

The 16S gene dataset consists of 454 FLX Titanium sequences spanning the V3 to V5 variable regions obtained for 190 samples (95 pairs). Detailed protocols used for 16S amplification and sequencing are available on the HMP Data Analysis and Coordination Center website (http://www.hmpdacc.org/tools_protocols.php). In brief, genomic DNA was subjected to 16S amplifications using primers designed incorporating the FLX Titanium adapters and a sample barcode sequence, allowing directional sequencing covering variable regions V5 to partial V3 (Primers: 357F 5'-CCTACGGGAGGCAGCAG-3' (SEQ ID NO:1) and 926R 5'CCGTCAATTCMTTTRAGT-3' (SEQ ID NO:2)). Polymerase chain reaction (PCR) mixtures (25 µl) contained 10 ng of template, 1× Easy A reaction buffer (Stratagene, La Jolla, Calif.), 200 mM of each dNTP (Stratagene), 200 nM of each primer, and 1.25U Easy A cloning enzyme (Stratagene). The cycling conditions for the V3-V5 consisted of an initial denaturation of 95° C. for 2 min, followed by 25 cycles of denaturation at 95° C. for 40 sec, annealing at 50° C. for 30 sec, extension at 72° C. for 5 min and a final extension at 72° C. for 7 min. Amplicons were confirmed on 1.2% Flash Gels (Lonza, Rockland, Me.) and purified with AMPure XP DNA purification beads (Beckman Coulter, Danvers, Mass.) according to the manufacturer and eluted in 25 µL of 1× low TE buffer (pH 8.0). Amplicons were quantified on Agilent Bioanalyzer 2100 DNA 1000 chips (Agilent Technologies, Santa Clara, Calif.) and pooled in equimolar concentration. Emulsion PCR and sequencing were performed according to the manufacturer's specifications.

Processing of 16S Sequence Data

Resulting sequences were processed using a data curation pipeline implemented in mothur (Schloss et al. 2009), complimented by abundantOTU (Ye 2010), and custom PERL scripts. Sequences were removed from the analysis if they were <200 nt or >600 nt, had a read quality score <25, contained ambiguous characters, had a non-exact barcode match, or did show more than four mismatches to the reverse primer sequences (926R). Remaining sequences were assigned to samples based on barcode matches, after which barcode and primer sequences were trimmed and reads were oriented such that all sequences begin with the 5' end according to standard sense strand conventions. All sequences were aligned using a NAST-based sequence aligner to a custom reference based on the SILVA alignment (Pruesse et al. 2007; Schloss et al. 2009). Chimeric sequences were identified using the mothur implementation of the ChimeraSlayer algorithm (Haas et al. 2011). Quality filtered and chimera-free sequences were clustered into Operational Taxonomic Units (OTU's) using abundantOTU (Ye 2010). Representative sequences per OTU were classified with the MSU RDP classifier v2.2 (Cole et al. 2009) using the taxonomy proposed by (Garrity et al. 2007), maintained at the Ribosomal Database Project (RDP 10 database, version 6).

Quantitative PCR Analysis

Quantitative real-time PCR was performed as described (Boutaga et al. 2005) using pan-*Fusobacterium* probe-primer sets as described (Boutaga et al. 2005). *Fusobacterium* quantitation was measured relative to human endogenous 18S (Applied Biosystems TaqMan® Ribosomal RNA Control Reagents, Hs99999901_s1 (part number 4331182)).

Microbial FISH Analysis

Frozen sections were fixed in Carnoy's solution overnight and embedded in paraffin, and 5 mm thick sections prepared and hybridized as previously described (Swidsinski et al. 2011). The sequences of the following FISH probes were obtained from probeBase (http://www.microbial-ecology.net/probebase/) (Loy et al. 2008): the "universal" bacterial probe-EUB338 (pB-00159), *Fusobacterium* targeted probe (pB-00782). Slides were imaged on an Olympus B40 microscope, digitally photographed using IP Lab. Composite z-stacks were assembled in IP Lab and composite photomicrographs were assembled in Adobe Photoshop.

Results

Figure 1A:
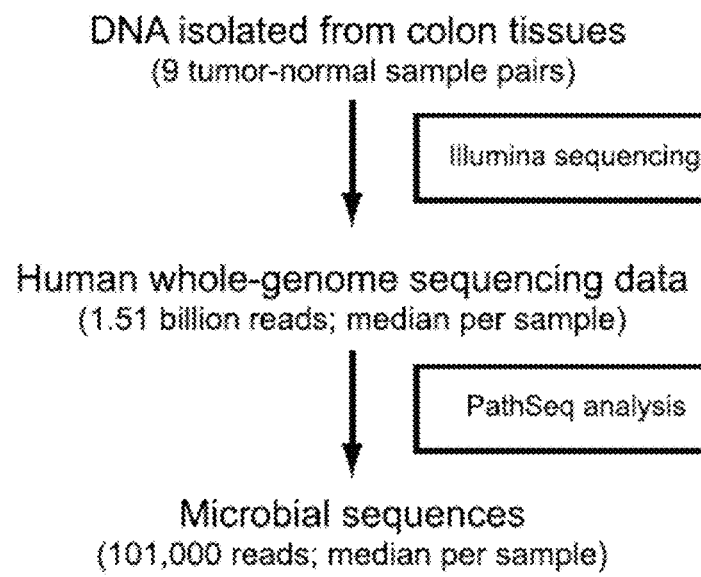
FIGS. 1A-D. Whole-genome sequencing analysis of the colorectal cancer microbiome. (1A) Schematic of experimental and computational whole-genome sequencing analysis workflow. (1B) Hierarchical clustering of phylotype relative abundance measurements demonstrates that microbial composition of tumor/normal pairs within individuals is more highly correlated than tumor/tumor pairs or normal/normal pairs from different individuals. Normal samples are shown in green, tumors are shown in purple. (1C) Linear Discriminant Analysis (LDA) coupled with effect size measurements identifies *Fusobacterium* as the most differentially abundant taxon in colon tumor versus normal specimens by whole-genome sequencing in 9 individuals. Tumor-enriched taxa are indicated with a positive LDA score (black), and taxa enriched in normal tissue have a negative score (gray). Only taxa meeting an LDA significant threshold of 1.8 are shown. (1D) Percent relative abundance for the genus *Fusobacterium* is depicted across all samples in the order of the labels in (B), demonstrating a tumor-enrichment in most individuals.

To determine the microbial composition of human colorectal cancer, whole genome sequences of nine colorectal cancers and matched normal colons (Bass et al.) were analyzed using PathSeq, a computational subtraction pipeline that culls out candidate microbial sequences (Kostic et al. 2011). These presumed bacterial sequences were identified by alignment to known sequenced microbial genomes (FIG. 1A). PathSeq analysis also identified the presence of virus sequences in these specimens including human herpesvirus 7, however no significant differences in viral sequence levels were detected between tumor and normal DNA.

Figure 1B:
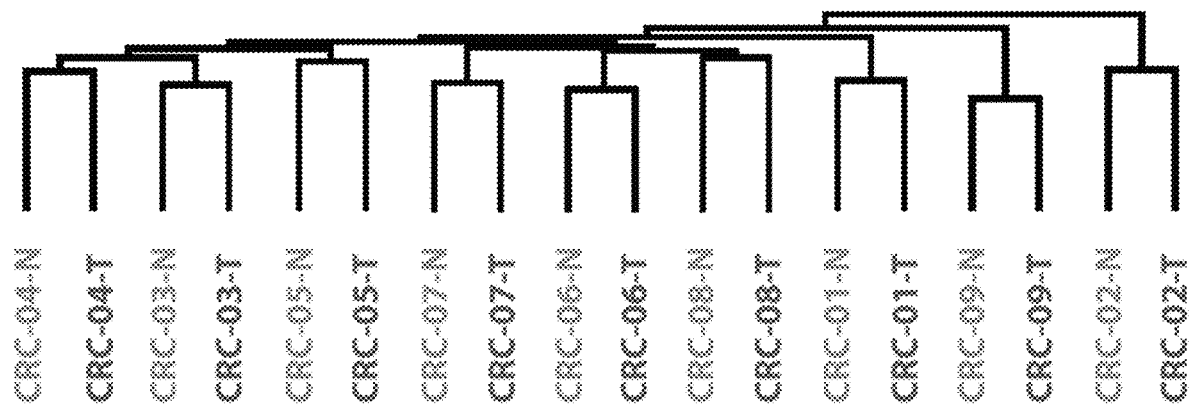

Hierarchical clustering analysis of the species-specific relative abundances of microbial sequences revealed that the microbial communities of a tumor and matched non-cancerous colon from a given patient were more similar to each other than are tumors or non-affected colon samples from different patients (FIG. 1B). This finding suggests that a patient's intestinal ecosystem may be more significant in shaping the microbiota than the microenvironment of a colon tumor or normal colonic tissue.

Figure 1C:
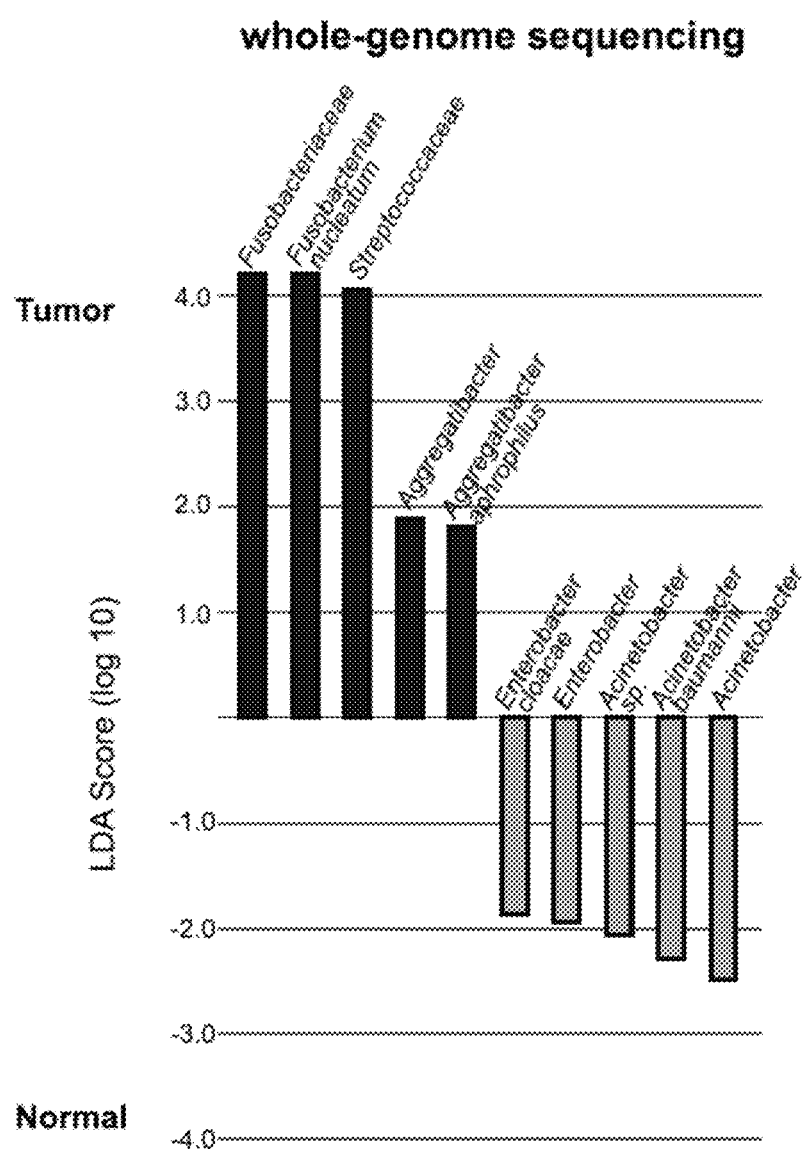
Figure 1D:
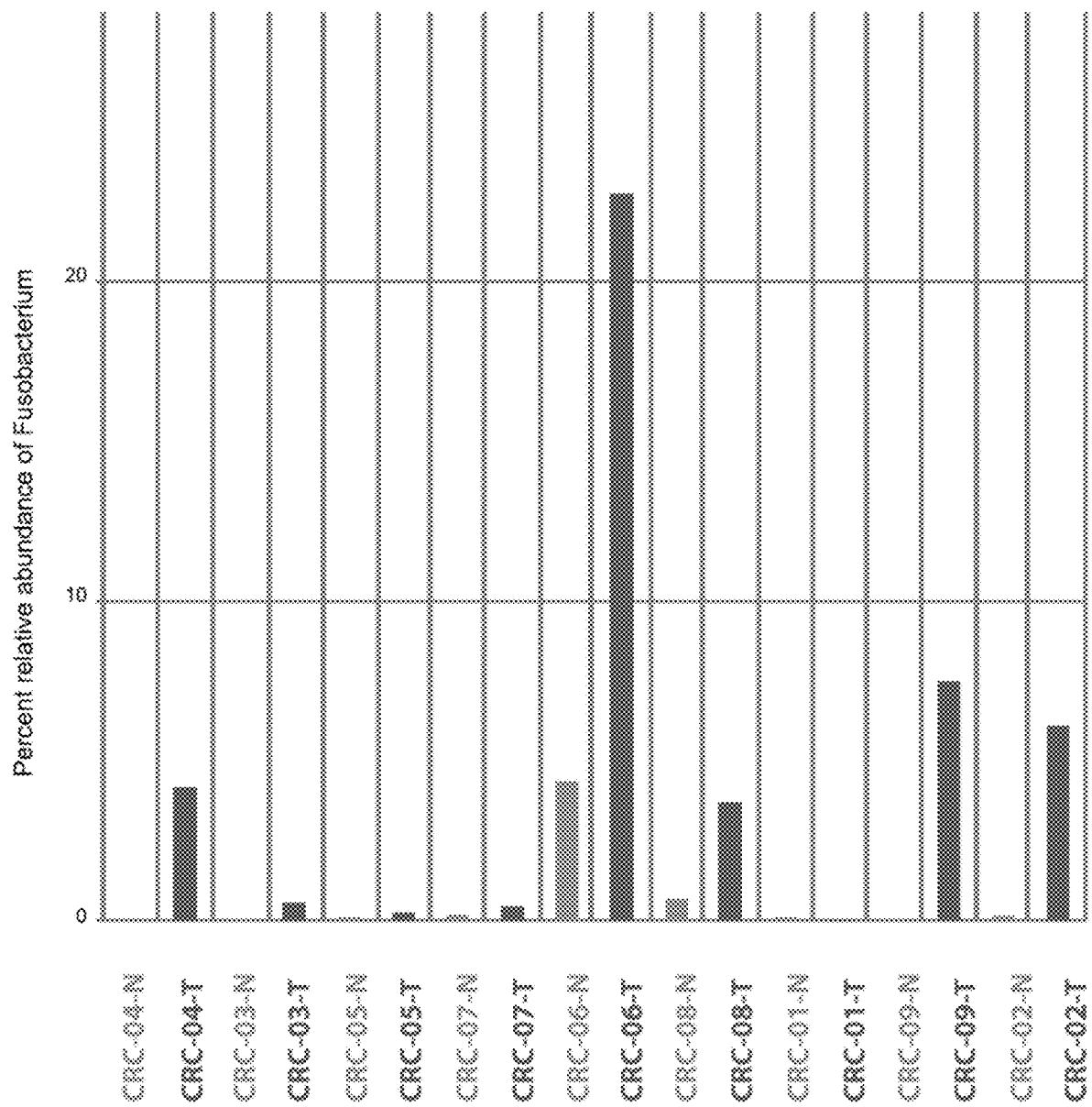

To identify bacterial species whose sequences are more abundant in colorectal tumors than in normal colon, a metagenomic biomarker discovery approach, LEfSe (Linear Discriminant Analysis (LDA) coupled with effect size measurements), which performs a non-parametric Wilcoxon sum-rank test followed by LDA analysis to assess the effect size of each differentially abundant taxon (Segata et al.), was applied. Using LEfSe, it was found that *Fusobacterium* sequences were significantly enriched in the colorectal cancer metagenomes as were sequences from the family of Streptococcaceae (FIG. 1C, FIG. 1D). Other taxa were enriched in tumor or normal tissue but their LDA enrichment scores were lower by 2 orders of magnitude or more (FIG. 1C). The high abundance of *Fusobacterium* sequences, ranging over 20% of total bacterial sequences, is a feature of some but not all colorectal cancer genomes (FIG. 1D).

Figure 2A:
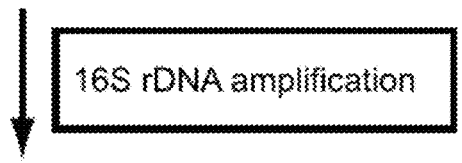
FIGS. 2A-F. 16S rDNA sequencing analysis of the colorectal cancer microbiome. (2A) Schematic of experimental and computational 16S rDNA sequencing analysis workflow. (2B) Beta-diversity distances calculated using phylotype relative abundance measurements between all pairs of samples demonstrate that the microbial composition of tumor/normal pairs within individuals is more highly correlated than tumor/tumor pairs, normal/normal pairs, or tumor/normal pairs from different individuals. (2C) Linear Discriminant Analysis (LDA) coupled with effect size measurements identifies *Fusobacterium* as the most differentially abundant taxon in colon tumor versus normal specimens by 16S rDNA sequencing in 95 individuals. Tumor-enriched taxa are indicated with a positive LDA score (black), and taxa enriched in normal tissue have a negative score (gray). Only taxa meeting an LDA significant threshold of 4.2 are shown. (2D) A cladogram representation of data in (2C). Tumor-enriched taxa are indicated with an asterisk. The brightness of each dot is proportional to its effect size. (2E) Absolute quantification of *Fusobacterium* DNA relative to a standard curve produced using *Fusobacterium nucleatum* genomic DNA and quantitative PCR probe specific to the *Fusobacterium* genus. P-value calculated by a Wilcoxon matched-pairs signed rank test (non-parametric). (2F) Quantification of *Fusobacterium* in tumor relative to normal by use of the $\Delta\Delta Ct$ method quantitated against a probe targeting human endogenous 18S.
Figure 2A:
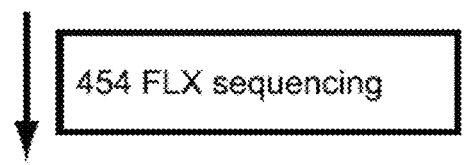
Figure 2B:
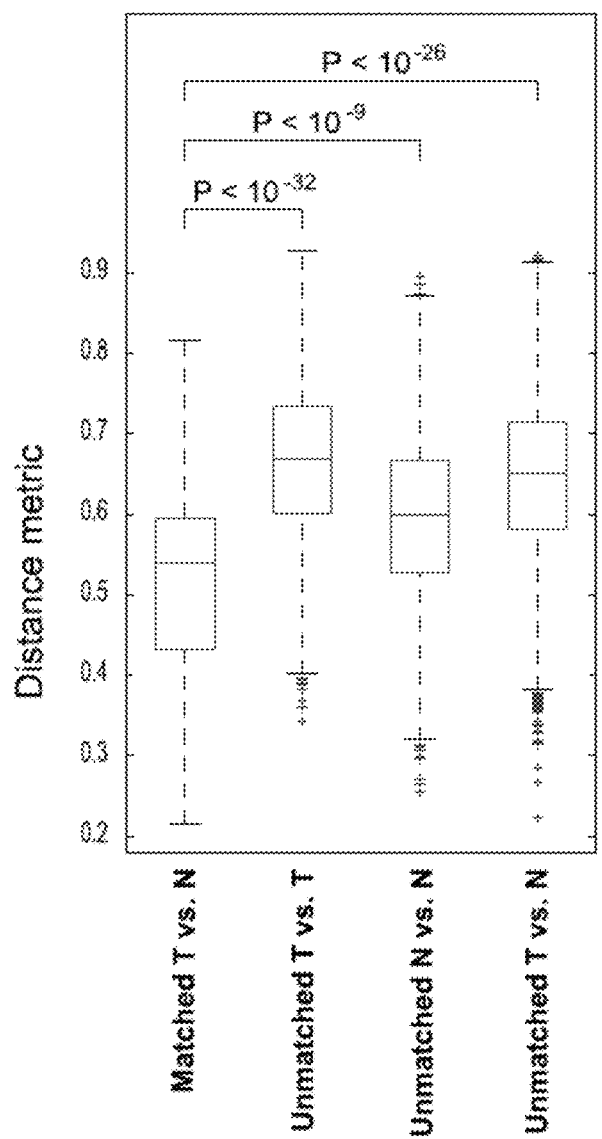
Figure 2C:
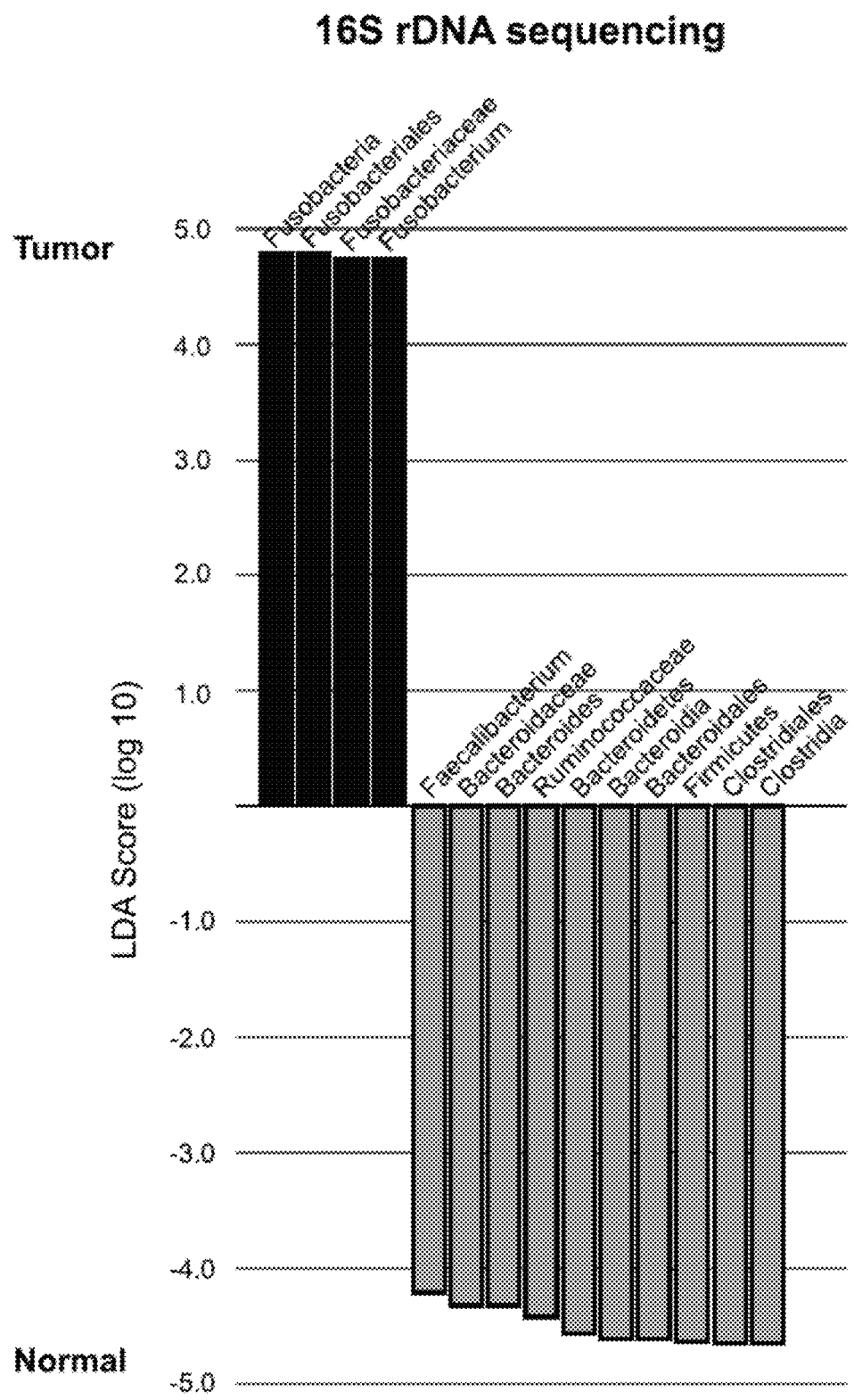
Figure 2D:
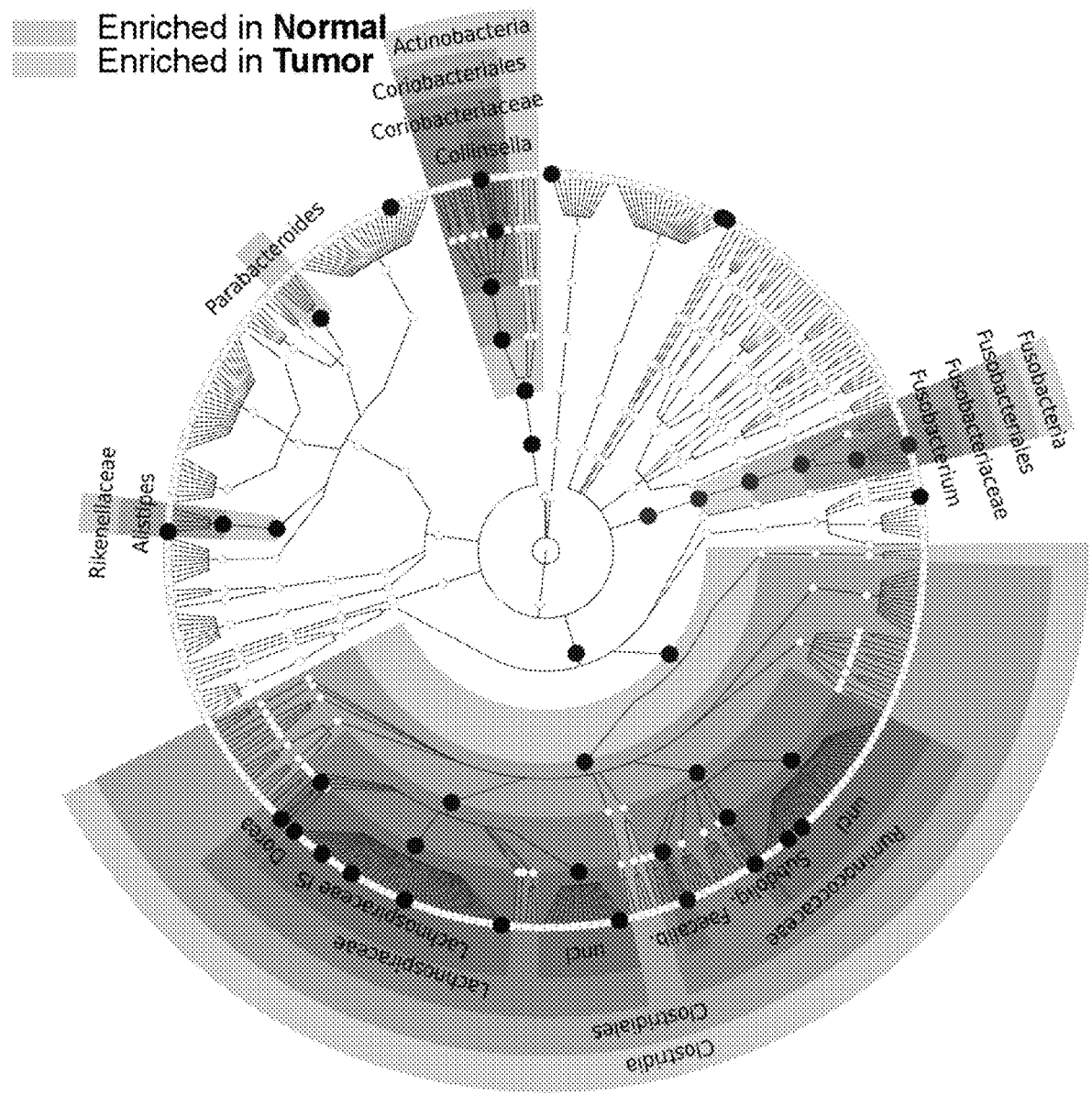

As the initial screen was performed on a sample size of 9 cases, a larger cohort of 95 paired specimens of colon cancer and normal colonic DNA was next examined to survey the colon cancer microbiome and validate the tumor-specific enrichment of *Fusobacterium*. Ribosomal 16S rDNA was amplified by PCR using consensus primers from 95 tumor/normal pairs, followed by picotiter-plate pyrosequencing to assess the relative abundance of DNA from bacterial and archaeal species (FIG. 2A). Overall, as was the case in the whole-genome sequence data, tumor/normal pairs from the same individual were much more highly correlated than tumor/tumor pairs or normal/normal pairs from different individuals (FIG. 2B). Colorectal tumors were associated with broad phylum-level changes including the depletion (i.e., reduced relative abundance) of *Firmicutes* and *Bacteroidetes*, most prominently the Clostridia (FIG. 2C, FIG. 2D); however the overall diversity in the tumors relative to adjacent tissue was not significantly differen). Consistent with the whole-genome sequencing results, the relative abundance of *Fusobacterium* was highly enriched in the population of tumor versus normal samples (FIG. 2C and FIG. 2D). However a tumor-enrichment for Streptococcaceae was not reproduced, most likely due to small sample-size in the initial whole-genome sequencing results. In addition, patient metadata was analyzed to identify correlations or possible confounding effects, but only a modest correlation with patient geographic location was found, as well as a correlation of higher microbial diversity with tumors of higher histological stage or grade.

Figure 2E:
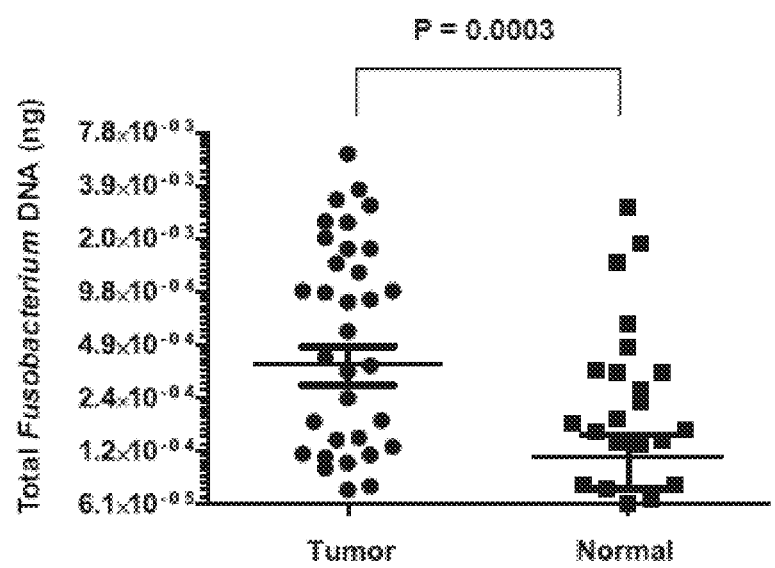
Figure 2F:
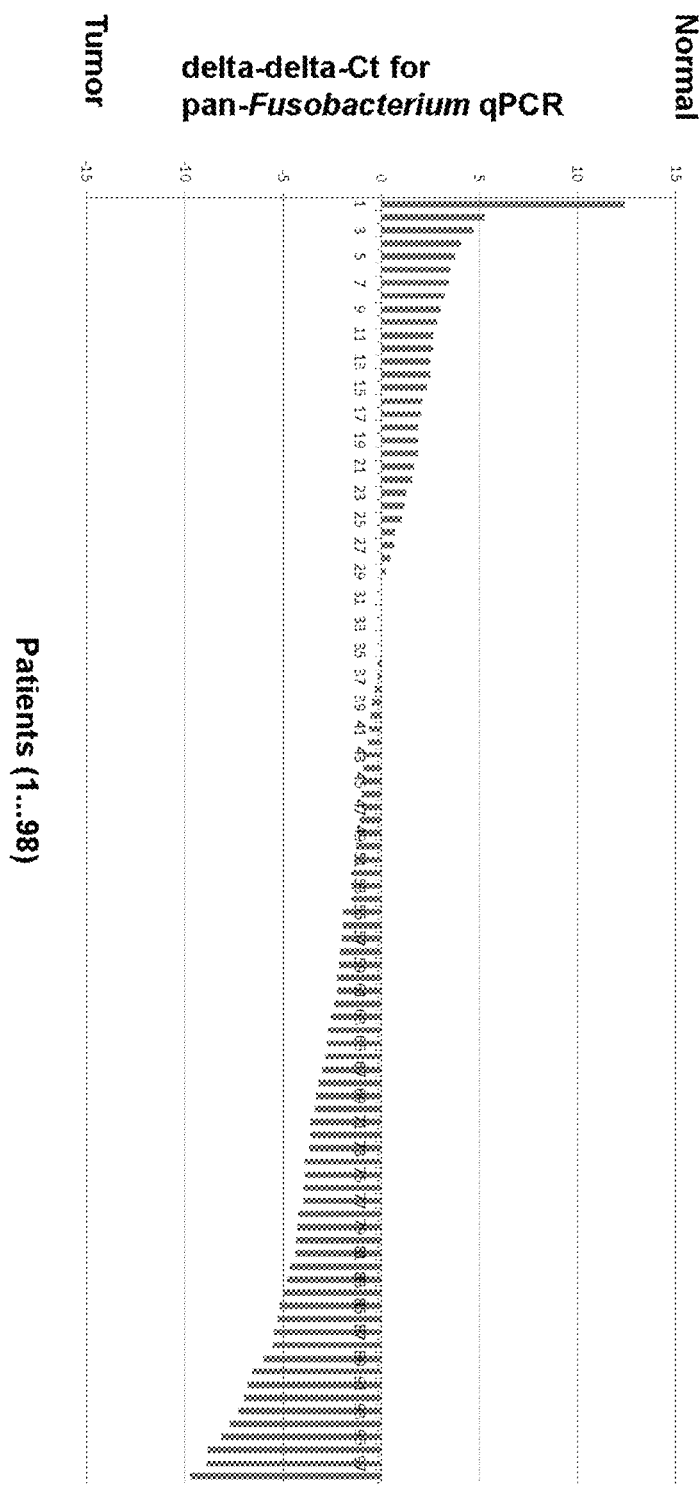

To determine if there was an absolute increase of *Fusobacterium* (as one possible explanation for enrichment is a depletion of other bacterial species in the tumor microenvironment) quantitative real-time PCR for *Fusobacterium* DNA performed relative to human DNA as a control. *Fusobacterium* DNA was enriched in the tumor relative to normal in 95 paired samples (FIGS. 2E-F).

As *Fusobacterium* species are enriched in colorectal cancer DNA and tissue, associations were sought that might suggest that fusobacteria are required for the survival or maintenance of colorectal cancer cells. Because *Fusobacterium* species can invade colonic epithelial cells (Strauss et al. 2011), colorectal cancer cell lines and hepatic and lymph node metastases were examined for evidence of fusobacterial DNA. Quantitative PCR analysis of 59 human colorectal cancer cell line DNAs revealed no significantly detectable *Fusobacterium* DNA, however these in vitro passaged cell lines are often cultured in the presence of antibiotics. Strikingly, however, when surgically resected colorectal cancer metastases were examined, *Fusobacterium* was detected in 2 out of 11 cases.

Figure 3:
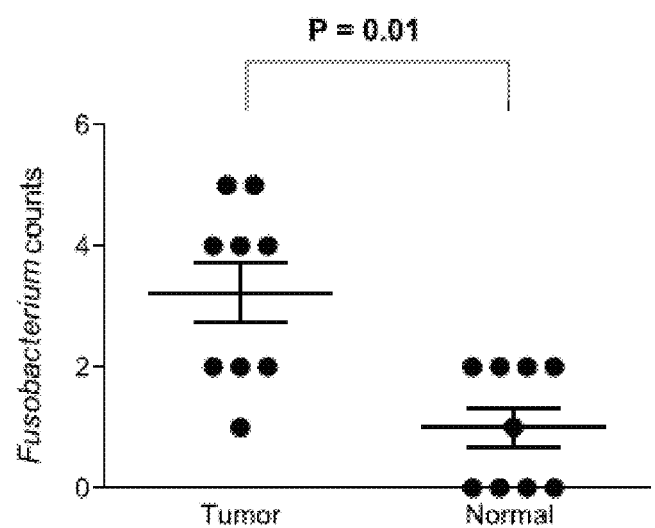
FIG. 3. Fluorescence in situ hybridization (FISH) detected enrichment of fusobacteria in colorectal tumors. FISH using an Oregon-Green 488-conjugated "universal bacterial" 16S rDNA-directed oligonucleotide probe (EUB338) and Cy3-conjugated *Fusobacterium* (FUSO) 16S rDNA-direct oligonucleotide probe demonstrated the presence of bacteria and *Fusobacterium* within in the colonic mucosa of colorectal tumor samples. Epithelial cell nuclei were stained with DAPI. To determine whether *Fusobacterium* was enriched in tumor versus normal pairs, 3 random 40× fields were chosen for scoring by an observer blinded to tumor/normal status, using selection criteria of mucosal tissue depth and a minimum of 5 bacteria visualized by the EUB338 probe per field. Each dot represents data from either a tumor or normal sample from 9 tumor/normal paired cases. The mean, SEM, and p-values (calculated by a Wilcoxon matched-pairs signed rank test) are shown.

Given the increased abundance of *Fusobacterium* sequences in colon cancer DNA, experiments were performed to determine whether *Fusobacterium* could be detected in histological sections of colon cancer, and if so, where. To address this question, 16S rDNA fluorescence in situ hybridization (FISH) oligonucleotide probes were used on colonic biopsy sections. Employing probeBase consortium 16S rDNA probes that detect the majority of bacteria (EUB338) and members of the genus *Fusobacterium* (FUSO) (Loy et al. 2008; Swidsinski et al. 2011), FISH analysis was performed on frozen (9 cases) and formalin-fixed paraffin embedded (12 cases) tissue sections from colorectal cancer and normal colon. The *Fusobacterium* probes detected bacteria in the colorectal cancer and normal tissue sections and were quantitated within the lamina propria and mucus; z-section stacks suggest that some of the imaged bacteria may reside intracellularly. Consistent with the analysis of *Fusobacterium* DNA described above, FISH-detected fusobacteria were enriched in the colorectal cancer compared to the normal samples (FIG. 3), in contrast to total bacteria counts which were more evenly distributed.

Figure 4B:
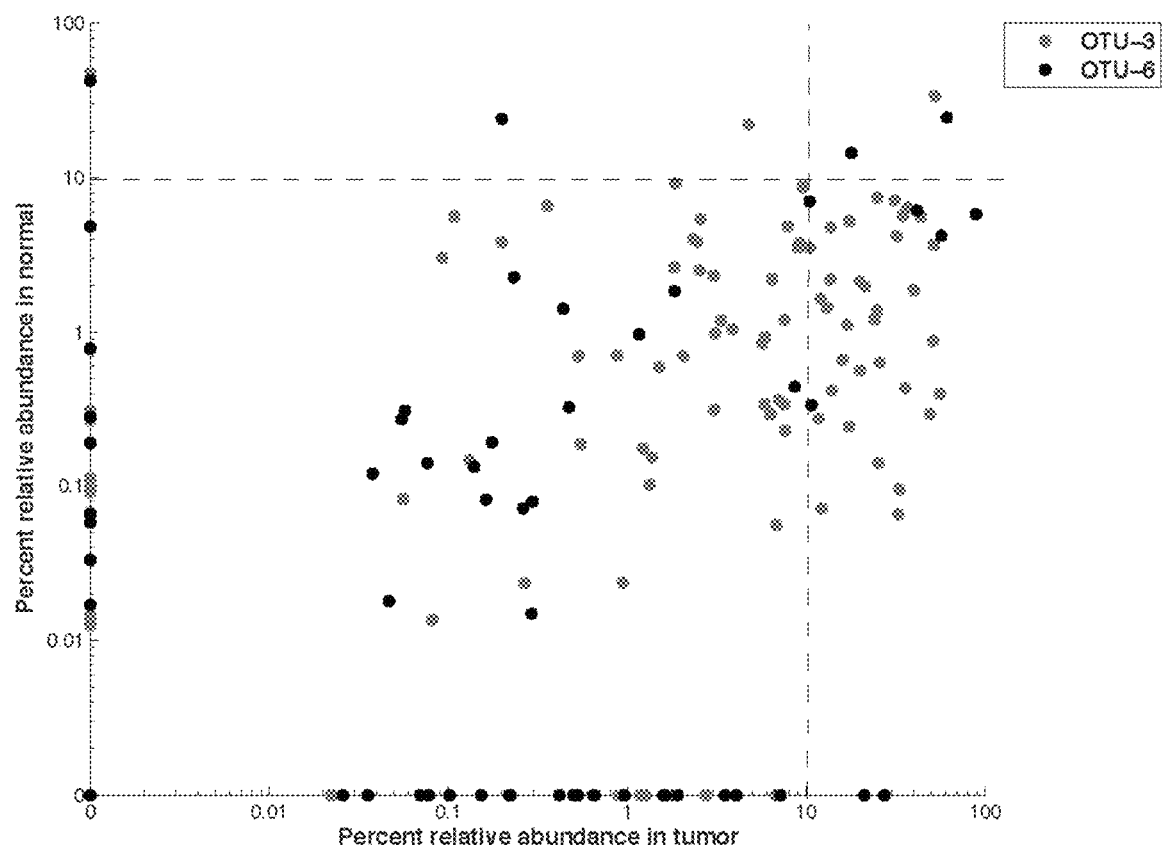

Finally, experiments were performed to assess the specific *Fusobacterium* species that are enriched in colorectal carcinomas. Based on the 16S ribosomal DNA sequences, 5 out of a total of 409 operational taxonomic units (OTUs, a proxy for species) identified in these samples were classified as members of the *Fusobacterium* genus. By performing multiple sequence alignments using these 5 OTUs along with 16S rDNA sequences from a reference set of 31 *Fusobacterium* species and constructing maximum likelihood trees, the OTUs were identified as most closely related to *Fusobacterium* nucleatum, *Fusobacterium* necrophorum, *Fusobacterium* mortiferum, and *Fusobacterium* perfoetens (FIG. 4A). The percent relative abundance in colorectal tumors versus normal colons of the two most abundant OTUs is shown in FIG. 4B, demonstrating that for most patients these OTUs are enriched in the tumor. Strikingly, only a subset of the cancers showed dramatic enrichment of *Fusobacterium* species, accounting for up to 89% of total bacterial DNA in some specimens; this result suggests that fusobacteria may be uniquely related to pathogenesis of subsets of colorectal cancer. The OTU with the greatest similarity to *F. nucleatum* was the most dominant phylotype identified within cancers, however some tumors contain more than one dominant species.

Example 2

*Fusobacterium* is More Abundant in Stool from Human CRC and Adenoma Cases than Healthy Individuals Given the enrichment of *Fusobacterium* spp. in colorectal tumor versus control colonic tissue, as demonstrated in Example 1, above, further experiments were performed to determine whether *Fusobacterium* spp. could be detected at higher levels in the gut microbiota of CRC patients relative to healthy controls in a case-control experiment. This example describes experiments in which the presence and abundance of *Fusobacterium* was determined in stool samples from human subjects with colorectal cancer and healthy control subjects.

Materials and Methods

The levels of *Fusobacterium* spp. 16S were compared to levels of universal Eubacteria 16S by quantitative PCR in stool. Stool was obtained from 27 individuals with colorectal carcinoma, 28 individuals with colonoscopy-confirmed adenoma, and 31 healthy individuals. DNA was isolated from each stool specimen by phenol-chloroform extraction. Quantitative real-time PCR was performed as described (Boutaga et al. FEMS Immunol Med Microbiol. 2005 Aug. 1; 45(2):191-9) using pan-*Fusobacterium* primer sets as described (Boutaga et al. 2005; Forward: GGATTTAT-TGGGCGTAAAGC (SEQ ID NO:3); Reverse: GGCAT-TCCTACAAATATCTACGAA (SEQ ID NO:4)). The oligonucleotide probe was labeled with the fluorescent reporter dyes 6-carboxyfluorescein at the 5' end and the quencher 6-carboxytetramethylrhodamine (TAMRA) at the 3' end (Probe: FAM-CTCTACACTTGTAGTTCCG-TAMRA (SEQ ID NO:5)). The expected amplicon size was 162 bp)).

Briefly, PCR amplification was performed in a total reaction mixture volume of 25 µl. The reaction mixtures contained 12.5 µl of 2× TaqMan universal PCR master mixture (PCR buffer, deoxynucleoside triphosphates, AmpliTaq Gold, an internal reference signal [6-carboxy-X-rhodamine], uracil N-glycosylase, $MgCl_2$; Applied Biosystems), 300 nM each *Fusobacterium* spp.-specific primer, 100 nM *Fusobacterium* spp.-specific probe, and 5 µl of purified DNA from the stool samples. Five microliters of the DNA extracted from *F. nucleatum* 7-1 was used to prepare the standard curve and as a positive control; the negative control was 5 µl of sterile $H_2O$.

The samples were subjected to an initial amplification cycle of 50° C. for 2 min and 95° C. for 10 min, followed by 45 cycles at 95° C. for 15 s and 60° C. for 1 min. The data were analyzed with ABI 7000 Sequence Detection System software.

The levels were normalized against a pan-Eubacteria primer set as previously described (Atarashi et al., Science 331:337-341 (2011); GGTGAATACGTTCCCGG (SEQ ID NO:6) and TACGGCTACCTTGTTACGACTT (SEQ ID NO:7)). *Fusobacterium* was found to be enriched in both colorectal cancer cases and colonic adenoma cases relative to the healthy cohort.

Results

As shown in FIG. 5, *Fusobacterium* is detected at a higher prevalence in stool from CRC and adenoma cases than healthy individuals (note that FIG. 5 is plotted on a log axis). Table 1 provides the numbers of samples in which *Fusobacterium* (Fuso) species were detected (+) or undetectable (−). *Fusobacterium* spp. were enriched in CRC patients (P<5e-05; Fisher's exact test). In this case, "undetectable" means a Fuso qPCR signal that was equivalent to the signal in the water negative control.

*Fusobacterium* spp. abundance was also determined in stool from patients with colonoscopy-confirmed colonic adenomas (FIG. 5 and Table 1). *Fusobacterium* spp. were again enriched in this patient group as compared to healthy control individuals, although there was a smaller statistical effect compared to CRC patients (P<5e-03; Fisher's exact test). This result was the first evidence that *Fusobacterium* spp. are enriched in patients with early colonic neoplasms.

TABLE 1

|  | Fuso (−) | Fuso (+) | Total |
|---|---|---|---|
| Normal | 16 | 15 | 31 |
| Adenoma | 4 | 24 | 28 |
| Carcinoma | 0 | 27 | 27 |

As compared to other screening modalities, with a sensitivity of 100% and a specificity of 52%, the present methods were more sensitive but less specific; see Table 2.

TABLE 2

| Test | Sensitivity/Specificity |
|---|---|
| Fecal occult blood testing, Hemoccult II | Sensitivity: 12.9-37.1% |
|  | Specificity: 97.7% |
| Fecal occult blood testing, Hemoccult SENSA | Sensitivity: 79.4% |
|  | Specificity: 86.7% |
| CT colonography | Sensitivity: 55-94% |
|  | Specificity: 91-96% |
| Fecal DNA mutation detection (APC, K-ras, DCC, p53) | Sensitivity: 52-91% |
|  | Specificity: 93-97% |
| Fecal DNA *Fusobacterium* detection | Sensitivity: 100% |
|  | Specificity: 52% |

Example 3

*Fusobacterium* Spp. Are Enriched in Patients with Early Colonic Neoplasms

Given the results, above, showing that *Fusobacterium* spp. are enriched in patients with early colonic neoplasms, experiments were performed to determine the prevalence of *Fusobacterium* spp. in paired adenoma tissue vs. adjacent normal tissue from human subjects.

Materials and Methods

DNA was extracted from human colonic adenoma tissues and matched adjacent normal colonic tissues from the same patient. Quantitative real-time PCR was performed as described (above and Boutaga et al. 2005).

Results

As shown in FIG. 6, *Fusobacterium* was found to be enriched in adenomas relative to adjacent normal tissues, suggesting that *Fusobacterium* is enriched in neoplasias prior to the development of carcinoma.

Example 4

Promotion of Tumorigenesis by Oral Inoculation of *Fusobacterium* Nucleatum into APC$^{Min+}$ Mice This example describes experiments using oral administration of the invasive strain *F. nucleatum* strain 7-1, originally isolated from the colon of an individual with inflammatory bowel disease (Strauss et al. 2011), which has been reported to exhibit pro-inflammatory potential (Dharmani et al., Infection and immunity, 2011. 79(7): p. 2597-607).

Materials and Methods $10^8$ CFU per day of *F. nucleatum* 7-1 (originally isolated from the lab Emma Allen-Vercoe, U. of Guelph; see Strauss et al., 2011) were administered orally for eight weeks to APC$^{Min+}$ mice, from weaning at d21 through d90 postnatal. These mice have a genetic predisposition to small intestinal and colonic tumors.

Results

Untreated, APC$^{Min+}$ mice normally develop colon tumors at about 6 months of age. In treated mice, the formation of tumors was observed at an early age (about three months after feeding *F. nucleatum* strain 7-1) (FIG. 7). IL-10$^{-/-}$ mice (Kuhn et al., Cell 75: 263-274 (1993)) and TRUC (T-bet$^{-/-}$× Rag2$^{-/-}$) mice (Garrett et al., Cell 131, 33-45 (2007)) did not exhibit colon tumors within this experimental timeframe. APC$^{min/+}$ mice did show an increased number of colon tumors relative to non-treated APC$^{min/+}$ littermates. The incidence of tumors was increased in the *F. nucleatum* fed mice compared to control mice in this study. These data suggest that *F. nucleatum* promotes carcinogenesis.

Example 5

*Fusobacterium* Nucleatum 7-1 is Enriched in Colon Tumor Tissues in Mice Fed *F. Nucleatum* 7-1

This Example describes experiments to determine whether *F. nucleatum* is also present in colon tumors present in mice fed *F. nucleatum* 7-1.

Materials and Methods

Colon tumors and matched adjacent normal tissues were resected from *F. nucleatum*-treated APC$^{min/+}$ mice. Briefly, DNA was extracted from the tissue and *F. nucleatum* abundance was quantified by quantitative real-time PCR as described above.

Results

The results, shown in FIG. 8, demonstrate enrichment in *F. nucleatum* in colon tumor tissues as compared to control normal colon tissues. This result parallels the human colonic tumor vs. adjacent normal *Fusobacterium* enrichment results described above.

REFERENCES

Bachrach G, Ianculovici C, Naor R, Weiss E I. 2005. Fluorescence based measurements of *Fusobacterium nucleatum* coaggregation and of fusobacterial attachment to mammalian cells. FEMS Microbiol Lett 248(2): 235-240.

Bass A J, Lawrence M S, Brace L E, Ramos A H, Drier Y, Cibulskis K, Sougnez C, Voet D, Saksena G et al. Genomic Sequencing of Colorectal Adenocarcinomas Identifies a Recurrent VTI1A-TCF7L2 Fusion. Nat Genet. 2011 Sep. 4; 43(10):964-8.

Boutaga K, van Winkelhoff A J, Vandenbroucke-Grauls C M, Savelkoul P H. 2005. Periodontal pathogens: a quantitative comparison of anaerobic culture and real-time PCR. FEMS Immunol Med Microbiol 45(2): 191-199.

Chang Y, Cesarman E, Pessin M S, Lee F, Culpepper J, Knowles D M, Moore P S. 1994. Identification of herpesvirus-like DNA sequences in AIDS-associated Kaposi's sarcoma. Science 266(5192): 1865-1869.

Cole J R, Wang Q, Cardenas E, Fish J, Chai B, Farris R J, Kulam-Syed-Mohideen A S, McGarrell D M, Marsh T, Garrity G M et al. 2009. The Ribosomal Database Project: improved alignments and new tools for rRNA analysis. Nucleic Acids Res 37(Database issue): D141-145.

Cover T L, Blaser M J. 2009. *Helicobacter pylori* in health and disease. Gastroenterology 136(6): 1863-1873.

Garrity G M, Lilburn T G, Cole J R, Harrison S H, Tindall B J. 2007. Taxonomic Outline of the Bacteria and Archaea. Taxonomic Outline of the Bacteria Release 7.

Goodman A L, Gordon J I. 2010. Our unindicted coconspirators: human metabolism from a microbial perspective. Cell Metab 12(2): 111-116.

Haas B J, Gevers D, Earl A M, Feldgarden M, Ward D V, Giannoukos G, Ciulla D, Tabbaa D, Highlander S K, Sodergren E et al. 2011. Chimeric 16S rRNA sequence formation and detection in Sanger and 454-pyrosequenced PCR amplicons. Genome Res 21(3): 494-504.

Han Y W, Shi W, Huang G T, Kinder Haake S, Park N H, Kuramitsu H, Genco R J. 2000. Interactions between periodontal bacteria and human oral epithelial cells: *Fusobacterium* nucleatum adheres to and invades epithelial cells. Infect Immun 68(6): 3140-3146.

Hope M E, Hold G L, Kain R, El-Omar E M. 2005. Sporadic colorectal cancer—role of the commensal microbiota. FEMS Microbiol Lett 244(1): 1-7.

Kostic A D, Ojesina I O, Pedamallu C S, Jung J, Verhaak R G W, Getz G, Meyerson M. 2011. PathSeq: software to identify or discover microbes by deep sequencing of human tissue. Nature Biotechnology 29(5): 4-7.

Loy A, Arnold R, Tischler P, Rattei T, Wagner M, Horn M. 2008. probeCheck—a central resource for evaluating oligonucleotide probe coverage and specificity. Environ Microbiol 10(10): 2894-2898.

Moore W E, Moore L V. 1994. The bacteria of periodontal diseases. Periodontol 2000 5: 66-77.

Neut C, Bulois P, Desreumaux P, Membre J M, Lederman E, Gambiez L, Cortot A, Quandalle P, van Kruiningen H, Colombel J F. 2002. Changes in the bacterial flora of the neoterminal ileum after ileocolonic resection for Crohn's disease. Am J Gastroenterol 97(4): 939-946.

Ohkusa T, Sato N, Ogihara T, Morita K, Ogawa M, Okayasu I. 2002. *Fusobacterium* varium localized in the colonic mucosa of patients with ulcerative colitis stimulates species-specific antibody. J Gastroenterol Hepatol 17(8): 849-853.

Polk D B, Peek R M, Jr. 2010. *Helicobacter pylori*: gastric cancer and beyond. Nat Rev Cancer 10(6): 403-414.

Pruesse E, Quast C, Knittel K, Fuchs B M, Ludwig W, Peplies J, Glockner F O. 2007. SILVA: a comprehensive online resource for quality checked and aligned ribosomal RNA sequence data compatible with ARB. Nucleic Acids Res 35(21): 7188-7196.

Rowland I R. 2009. The role of the gastrointestinal microbiota in colorectal cancer. Curr Pharm Des 15(13): 1524-1527.

Schloss P D, Westcott S L, Ryabin T, Hall J R, Hartmann M, Hollister E B, Lesniewski R A, Oakley B B, Parks D H, Robinson C J et al. 2009. Introducing mothur: open-source, platform-independent, community-supported software for describing and comparing microbial communities. Appl Environ Microbiol 75(23): 7537-7541.

Sears C L, Pardoll D M. 2011. Perspective: alpha-bugs, their microbial partners, and the link to colon cancer. J Infect Dis 203(3): 306-311.

Segata N, Izard J, Waldron L, Gevers D, Miropolsky L, Garrett W S, Huttenhower C. Metagenomic biomarker discovery and explanation. Genome Biol. 2011 Jun. 24; 12(6):R60.

Strauss J, Kaplan G G, Beck P L, Rioux K, Panaccione R, Devinney R, Lynch T, Allen-Vercoe E. 2011. Invasive potential of gut mucosa-derived *Fusobacterium* nucleatum positively correlates with IBD status of the host. Inflamm Bowel Dis. 17, 1971-1978.

Swidsinski A, Dorffel Y, Loening-Baucke V, Theissig F, Ruckert J C, Ismail M, Rau W A, Gaschler D, Weizenegger M, Kuhn S et al. 2011. Acute appendicitis is characterised by local invasion with *Fusobacterium* nucleatum/necrophorum. Gut 60(1): 34-40.

Uitto V J, Baillie D, Wu Q, Gendron R, Grenier D, Putnins E E, Kanervo A, Firth J D. 2005. *Fusobacterium* nucleatum increases collagenase 3 production and migration of epithelial cells. Infect Immun 73(2): 1171-1179.

Yang L, Pei Z. 2006. Bacteria, inflammation, and colon cancer. World J Gastroenterol 12(42): 6741-6746.

Ye Y. 2010. Fast and accurate identification and quantification of abundant species from pyrosequences of 16S rRNA by consensus alignment. The Proceedings of BIBM 153.

zur Hausen H. 2009. Human papillomavirus & cervical cancer. Indian J Med Res 130(3): 209.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of delaying progression or development of colorectal cancer in a subject in need thereof, the method comprising:
   a) obtaining a sample comprising colorectal tumor tissue and/or a stool sample from a subject who has colorectal cancer;
   b) detecting a level of Fusobacteria in the sample using polymerase chain reaction (PCR);
   c) administering an effective amount of a beta-lactam or a nitroimidazole to the subject if the level of Fusobacteria in the sample is higher than a reference level of Fusobacteria obtained from a subject without colorectal cancer; and
   d) delaying progression or development of the colorectal cancer in the subject by decreasing the level of Fusobacteria in the subject's colon.

2. The method of claim 1, wherein the level of Fusobacteria in the sample is detected using quantitative PCR.

3. The method of claim 1, wherein the beta-lactam is selected from the group consisting of a penicillin, a cephalosporin, a monobactam, and a carbapenem.

4. The method of claim 1, wherein the nitroimidazole is selected from the group consisting of metronidazole, tinidazole, and nimorazole.

5. The method of claim 1, wherein the beta-lactam or the nitroimidazole is administered systemically.

6. The method of claim 1, wherein the beta-lactam or the nitroimidazole is administered in an oral composition formulated for delivery to the subject's colon.

7. The method of claim 1, wherein the beta-lactam or the nitroimidazole is administered rectally.

8. The method of claim 1, wherein the subject is a human subject.

9. The method of claim 1, wherein the Fusobacteria is *Fusobacterium nucleatum*.

10. A method of delaying progression or development of colorectal cancer in a subject in need thereof, the method comprising:
    a) obtaining a sample comprising colorectal tumor tissue and/or a stool sample from a subject who has colorectal cancer;
    b) detecting a level of Fusobacteria in the sample using polymerase chain reaction (PCR);
    c) administering an effective amount of a beta-lactam or a nitroimidazole to the subject if the level of Fusobacteria in the sample is higher than a reference level of Fusobacteria obtained from a subject without a Fusobacteria infection; and
    d) delaying progression or development of the colorectal cancer in the subject by decreasing the level of Fusobacteria in the subject's colon.

11. The method of claim 10, wherein the level of Fusobacteria in the sample is detected using quantitative PCR.

12. The method of claim 10, wherein the beta-lactam is selected from the group consisting of a penicillin, a cephalosporin, a monobactam, and a carbapenem.

13. The method of claim 10, wherein the nitroimidazole is selected from the group consisting of metronidazole, tinidazole, and nimorazole.

14. The method of claim 10, wherein the beta-lactam or the nitroimidazole is administered systemically.

15. The method of claim 10, wherein the beta-lactam or the nitroimidazole is administered in an oral composition formulated for delivery to the subject's colon.

16. The method of claim 10, wherein the beta-lactam or the nitroimidazole is administered rectally.

17. The method of claim 10, wherein the subject is a human subject.

18. The method of claim 10, wherein the Fusobacteria is *Fusobacterium nucleatum*.

* * * * *

UNITED STATES PATENT AND TRADEMARK OFFICE
CERTIFICATE OF CORRECTION

| | |
|---|---|
| PATENT NO. | : 11,060,148 B2 |
| APPLICATION NO. | : 14/054494 |
| DATED | : July 13, 2021 |
| INVENTOR(S) | : Matthew Meyerson and Aleksandar Kostic |

It is certified that error appears in the above-identified patent and that said Letters Patent is hereby corrected as shown below:

In the Specification

Please delete the paragraph after the heading "FEDERALLY SPONSORED RESEARCH OR DEVELOPMENT" at Column 1, Lines 11-14:
"This invention was made with Government support under Grant No. RC2CA148317 awarded by the National Institutes of Health. The Government has certain rights in the invention."

And replace with the following paragraph:
This invention was made with government support under Grant Nos. CA127003, CA148317, and HG003067 awarded by the National Institutes of Health. The government has certain rights in the invention.

Signed and Sealed this
Twenty-fifth Day of June, 2024

Katherine Kelly Vidal
*Director of the United States Patent and Trademark Office*